(12) United States Patent
Schuman, Sr. et al.

(10) Patent No.: US 9,235,979 B2
(45) Date of Patent: Jan. 12, 2016

(54) USER STATION FOR HEALTHCARE COMMUNICATION SYSTEM

(71) Applicant: Hill-Rom Services, Inc., Batesville, IN (US)

(72) Inventors: Richard J. Schuman, Sr., Cary, NC (US); Erik E. Roehl, Apex, NC (US); Williams F. Collins, Jr., Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 14/453,009

(22) Filed: Aug. 6, 2014

(65) Prior Publication Data

US 2014/0347174 A1  Nov. 27, 2014

Related U.S. Application Data

(63) Continuation of application No. 13/908,062, filed on Jun. 3, 2013, now Pat. No. 8,803,669, which is a continuation of application No. 13/444,516, filed on Apr. 11, 2012, now Pat. No. 8,456,286, which is a continuation of application No. 12/369,832, filed on Feb. 12, 2009, now Pat. No. 8,169,304.

(60) Provisional application No. 61/066,877, filed on Feb. 22, 2008, provisional application No. 61/066,918, filed on Feb. 22, 2008, provisional application No. 61/145,306, filed on Jan. 16, 2009.

(51) Int. Cl.
| | | |
|---|---|---|
| *G08B 5/22* | (2006.01) | |
| *G08B 25/00* | (2006.01) | |
| *G08B 7/06* | (2006.01) | |
| *H04L 29/08* | (2006.01) | |
| *G08B 25/01* | (2006.01) | |
| *A61B 5/00* | (2006.01) | |

(52) U.S. Cl.
CPC ............ *G08B 25/00* (2013.01); *A61B 5/002* (2013.01); *A61B 5/7465* (2013.01); *G08B 5/222* (2013.01); *G08B 7/06* (2013.01); *G08B 25/016* (2013.01); *H04L 67/12* (2013.01); *H04L 67/18* (2013.01)

(58) Field of Classification Search
CPC .... G06Q 50/22; G06Q 50/24; G06F 19/3418; G08B 25/00; G08B 25/016; G08B 7/06; G08B 5/222; H04L 67/12; H04L 67/18; A61B 5/002; A61B 5/7465
USPC .................. 340/286.07, 691.6, 692
See application file for complete search history.

(56) References Cited

U.S. PATENT DOCUMENTS

| | | |
|---|---|---|
| 2,330,356 A | 9/1943 | Belliveau |
| 2,335,524 A | 11/1943 | Lomax |

(Continued)

FOREIGN PATENT DOCUMENTS

| | | |
|---|---|---|
| EP | 1 623 666 A2 | 2/2006 |
| EP | 1 679 648 | 7/2006 |

(Continued)

OTHER PUBLICATIONS

Hill-Rom A Hillenbrand Industry, The COMposer® System Installation Manual, 2003.

(Continued)

*Primary Examiner* — Thomas Mullen
(74) *Attorney, Agent, or Firm* — Barnes & Thornburg LLP

(57) ABSTRACT

A user station configurable for use in a healthcare communication system, such as a nurse call system, is provided.

16 Claims, 25 Drawing Sheets

(56) References Cited

U.S. PATENT DOCUMENTS

| | | |
|---|---|---|
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Ghahariiran |
| 4,907,845 A | 3/1990 | Wood |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,075,523 A | 12/1991 | Ford |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,140,309 A | 8/1992 | Gusakov |
| 5,153,584 A | 10/1992 | Engira |
| 5,235,258 A | 8/1993 | Schuerch |
| 5,266,944 A | 11/1993 | Carroll et al. |
| 5,276,680 A | 1/1994 | Messenger |
| 5,291,399 A | 3/1994 | Chaco |
| 5,319,355 A | 6/1994 | Russek |
| 5,319,363 A | 6/1994 | Welch et al. |
| 5,327,592 A | 7/1994 | Stump |
| 5,351,439 A | 10/1994 | Takeda et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,430,900 A | 7/1995 | Kim |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,511,256 A | 4/1996 | Capaldi |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,564,108 A | 10/1996 | Hunsaker et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,600,214 A | 2/1997 | Fromson |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,649,833 A | 7/1997 | Pfeuffer et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II et al. |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,714,548 A | 2/1998 | Ma et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,781,921 A | 7/1998 | Nichols |
| 5,787,528 A | 8/1998 | Antinori |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,901,391 A | 5/1999 | Kato |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,956,539 A | 9/1999 | Fitterman et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |

(56) References Cited

U.S. PATENT DOCUMENTS

| | | |
|---|---|---|
| 6,037,723 A | 3/2000 | Shafer et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,101,644 A | 8/2000 | Gagneur et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,221,012 B1 | 4/2001 | Maschke et al. |
| 6,241,668 B1 | 6/2001 | Herzog |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,483,264 B1 | 11/2002 | Shafer et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,105 B2 | 4/2003 | Chea, Jr. et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,224 B1 | 5/2003 | Kung et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,358 B1 | 12/2003 | Odagiri |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,693,513 B2 | 2/2004 | Tuttle |
| 6,693,514 B2 | 2/2004 | Perea, Jr. et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,607 B2 | 7/2004 | Engler |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,788,206 B1 | 9/2004 | Edwards |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,864,795 B2 | 3/2005 | Smith et al. |
| 6,868,256 B2 | 3/2005 | Dooley et al. |
| 6,870,484 B1 | 3/2005 | Brinsfield et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,892,083 B2 | 5/2005 | Shostak |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 6,968,375 B1 | 11/2005 | Brown |
| 6,982,639 B2 | 1/2006 | Brackett et al. |
| 6,988,989 B2 | 1/2006 | Weiner et al. |
| 6,998,986 B2 | 2/2006 | Smith |
| 7,020,921 B2 | 4/2006 | Wang |
| 7,023,821 B2 | 4/2006 | Wotherspoon et al. |
| 7,038,584 B2 | 5/2006 | Carter |
| 7,053,767 B2 | 5/2006 | Petite et al. |
| 7,061,396 B1 | 6/2006 | Conrad et al. |

(56) References Cited

U.S. PATENT DOCUMENTS

| | | |
|---|---|---|
| 7,068,143 B2 | 6/2006 | Doering et al. |
| 7,071,820 B2 | 7/2006 | Callaway |
| 7,079,036 B2 | 7/2006 | Cooper et al. |
| 7,088,235 B1 | 8/2006 | Carricut |
| 7,092,376 B2 | 8/2006 | Schuman |
| 7,107,642 B2 | 9/2006 | Wong et al. |
| 7,138,902 B2 | 11/2006 | Menard |
| 7,151,457 B2 | 12/2006 | Riley et al. |
| 7,160,133 B2 | 1/2007 | Karadimas et al. |
| 7,248,881 B2 | 7/2007 | Shostak |
| 7,263,669 B2 | 8/2007 | Denholm |
| 7,275,220 B2 | 9/2007 | Brummel et al. |
| 7,290,299 B2 | 11/2007 | Votel |
| 7,292,135 B2 | 11/2007 | Bixler et al. |
| 7,299,512 B2 | 11/2007 | Cavalier et al. |
| 7,301,451 B2 | 11/2007 | Hastings |
| 7,307,522 B2 | 12/2007 | Dawson |
| 7,310,541 B2 | 12/2007 | Shostak |
| 7,319,386 B2 | 1/2008 | Collins, Jr. et al. |
| 7,333,002 B2 | 2/2008 | Bixler et al. |
| 7,336,187 B2 | 2/2008 | Hubbard, Jr. et al. |
| 8,169,304 B2 | 5/2012 | Schuman, Sr. et al. |
| 8,456,286 B2 | 6/2013 | Schuman et al. |
| 8,803,669 B2 | 8/2014 | Schuman, Sr. et al. |
| 2001/0044823 A1 | 11/2001 | Labounty et al. |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0101349 A1 | 8/2002 | Rojas, Jr. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0009330 A1 | 1/2003 | Cho |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0179099 A1 | 9/2003 | Perea, Jr. et al. |
| 2003/0197614 A1 | 10/2003 | Smith et al. |
| 2003/0206116 A1 | 11/2003 | Weiner et al. |
| 2003/0212575 A1 | 11/2003 | Saalsaa et al. |
| 2003/0230469 A1 | 12/2003 | Engler |
| 2004/0064890 A1 | 4/2004 | Kim et al. |
| 2004/0158922 A1 | 8/2004 | Eberler et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0222897 A1 | 11/2004 | Schuhmann et al. |
| 2004/0243446 A1 | 12/2004 | Wyatt |
| 2004/0249670 A1 | 12/2004 | Noguchi et al. |
| 2004/0261184 A1 | 12/2004 | Flick |
| 2005/0035862 A1 | 2/2005 | Wildman et al. |
| 2005/0055779 A1 | 3/2005 | Damewood |
| 2005/0076441 A1 | 4/2005 | Dominati et al. |
| 2005/0110617 A1 | 5/2005 | Kile et al. |
| 2005/0155149 A1 | 7/2005 | Pedersen |
| 2005/0168341 A1 | 8/2005 | Reeder et al. |
| 2005/0170863 A1 | 8/2005 | Shostak |
| 2005/0206505 A1 | 9/2005 | Arcaria |
| 2005/0242946 A1 | 11/2005 | Hubbard et al. |
| 2006/0046579 A1 | 3/2006 | Karadimas et al. |
| 2006/0049936 A1 | 3/2006 | Collins et al. |
| 2006/0114854 A1 | 6/2006 | Wotherspoon et al. |
| 2006/0126560 A1 | 6/2006 | Wotherspoon et al. |
| 2006/0136265 A1 | 6/2006 | Summers et al. |
| 2006/0214786 A1 | 9/2006 | Bixler et al. |
| 2006/0220798 A1 | 10/2006 | Willis |
| 2006/0239195 A1 | 10/2006 | Camins et al. |
| 2006/0248221 A1 | 11/2006 | Hottel et al. |
| 2006/0267740 A1 | 11/2006 | Bixler et al. |
| 2007/0071114 A1 | 3/2007 | Sanderford, Jr. et al. |
| 2007/0135688 A1 | 6/2007 | Brown |
| 2007/0156456 A1 | 7/2007 | McGillin et al. |
| 2007/0210917 A1 | 9/2007 | Collins et al. |
| 2007/0229249 A1 | 10/2007 | McNeal et al. |
| 2007/0237487 A1 | 10/2007 | Lin |
| 2007/0239484 A1 | 10/2007 | Arond et al. |
| 2007/0293745 A1 | 12/2007 | McCutcheon et al. |
| 2008/0004904 A1 | 1/2008 | Tran |
| 2008/0015900 A1 | 1/2008 | Denholm |
| 2008/0027754 A1 | 1/2008 | Auker et al. |
| 2012/0194327 A1 | 8/2012 | Schuman et al. |
| 2013/0257600 A1 | 10/2013 | Schuman, Sr. et al. |

FOREIGN PATENT DOCUMENTS

| | | |
|---|---|---|
| GB | 250 769 | 4/1926 |
| JP | 1-76197 | 3/1989 |
| WO | WO 02/091297 | 11/2002 |
| WO | WO 2004/036390 | 4/2004 |

OTHER PUBLICATIONS

Hill-Rom A Hillenbrand Industry, The COMposer Communication System Service Manual, 1995.
Hill-Rom A Hillenbrand Industry, COMLinx™ Enterprise Solutions Nurse Communication Module, User's Guide, 2000.
GE Telligence™ System Overview (5 pages).
European Search Report for EP 09 25 0419, dated Aug. 13, 2010, (7 pages).
Partial European Search Report from EP 09 25 0420 dated Jun. 16, 2009.
(Online) XP002530934 Hill-Rom Technical Brief,www.hill-rom/Canada/PDF/144097.pdf. "CONLinx Nurse Communication Module Technological Advances", Jul. 13, 2006, 4 pages.
Extended European Search Report for EP 09 25 0421.6, dated Nov. 15, 2013, 10 pages.
EP Search Report and Opinion for Application No./U.S. Pat. No. 09250427.3-1972 / 2093988, dated Mar. 16, 2015 (11 pages).

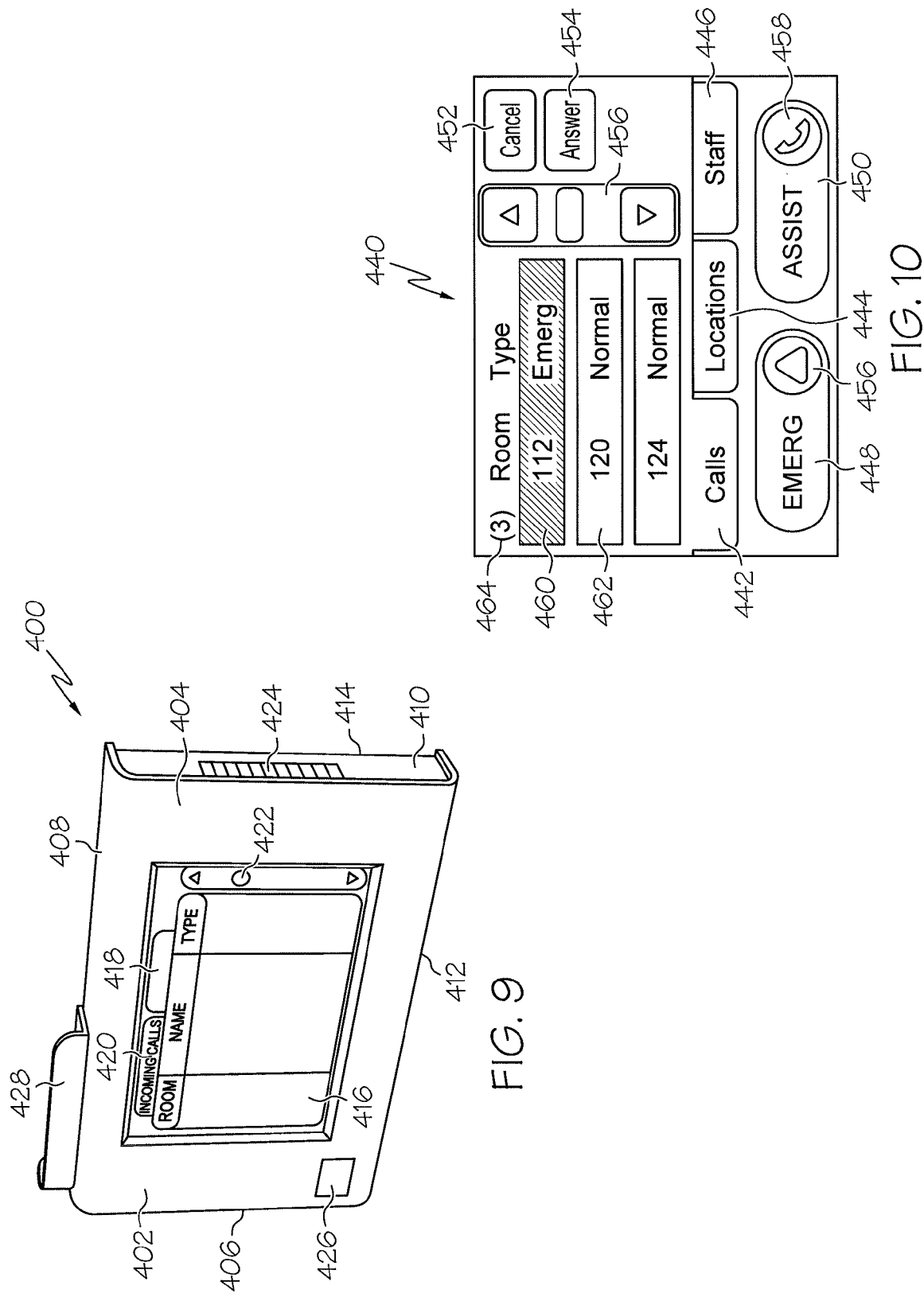

USER STATION FOR HEALTHCARE COMMUNICATION SYSTEM

CROSS-REFERENCE TO RELATED APPLICATIONS

This application is a continuation of U.S. application Ser. No. 13/908,062, filed Jun. 3, 2013, issued as U.S. Pat. No. 8,803,669, which is a continuation of U.S. application Ser. No. 13/444,516, filed Apr. 11, 2012, issued as U.S. Pat. No. 8,456,286, which is a continuation of U.S. application Ser. No. 12/369,832, filed Feb. 12, 2009, issued as U.S. Pat. No. 8,169,304, which claims the benefit of U.S. Provisional Application Nos. 61/066,882 filed Feb. 22, 2008, 61/066,877 filed Feb. 22, 2008, 61/066,883 filed Feb. 22, 2008, 61/066,918, filed Feb. 22, 2008, and 61/145,306, filed Jan. 16, 2009, all of which are hereby incorporated herein by this reference in their entirety.

BACKGROUND

The present disclosure relates generally to healthcare communication systems such as patient-nurse communication systems, and more particularly to user stations usable in connection with such systems.

Healthcare communication systems such as patient-nurse communication systems or "nurse call" systems enable communication among members of a nursing staff and other persons dispersed throughout a healthcare facility. Such systems generally provide information about the current status or condition of patients in the facility, and enable voice communication between patients and staff members through a telecommunications infrastructure.

One example of a known nurse call system that includes a user station is Hill-Rom's COMLINX® system. In the COMLINX® system, a "master station" is provided, which is configured to oversee the operation of the system for a specific territory within a facility, such as a nursing unit or units or the entire facility. The master station communicates call information to audio stations that are positioned at various locations throughout the monitored territory. Types of audio stations include patient stations (also called "room stations"), which are located in patient rooms, and staff stations, which are located in designated staff areas. The prior art audio stations have more limited functionality than a master station. For instance, prior art audio stations generally provide for viewing call information in a limited fashion, placing calls, answering unanswered calls, and canceling calls originating from the location in which the audio station is installed.

There is still a need for advanced healthcare communication system capabilities directed to improving nursing staff and overall hospital efficiency. Additional or improved features that are directed to reducing the risk of adverse patient conditions occurring in the facility are also needed. However, as cost is often a concern to these facilities, advancements that can be achieved while containing or reducing the costs of implementing, maintaining and operating these systems are desired.

SUMMARY

This disclosure describes a user station for a patient-nurse communication system.

In one embodiment, a user station for a patient-nurse communication system includes a housing defining an interior region, where the housing is positionable in a patient room of a healthcare facility. The user station also includes at least one communications port coupled to the housing. The communications port is configured to operably couple the user station to a patient-nurse communication system. The user station also includes a graphical display supported by the housing, and electrical circuitry in the housing. The electrical circuitry is configured to associate the user station with the patient room, receive calls from the patient-nurse communication system that relate to the patient room, and display information relating to the received calls on the graphical display.

The electrical circuitry may be configured to display first and second windows on the graphical display, and to display the information relating to the received calls in the first window. The electrical circuitry may be configured to display staff information and/or patient information in the second window.

The user station may include a user control coupled to the housing and configured to enable a user to manipulate the graphical display of received calls. The user control is configured to enable a user to answer a received call.

The electrical circuitry may include computer componentry configured to play pre-recorded audio files at the user station in response to a received call.

The graphical display may be configured to display visual cues relating to at least one of the received calls. The graphical display may be configured to display a first visual cue relating to a first received call in a first color and display a second visual cue relating to a second received call in a second color. One or more of the visual cues may include a graphical icon.

The communications port may include computer componentry configured to connect the user station to a Power over Ethernet network switch. The graphical display may include a touchscreen comprising at least one of a high resolution touch display, a Super Video Graphics Array (SVGA) display, and at least one touch actuator.

The electrical circuitry may include computer componentry configured to enable a user to place calls to other users of the patient-nurse communication system and select a preferred method of calling other users from a plurality of calling methods including voice routing to a located position, wireless telephone, and/or text paging to a wireless device.

The user station may include a microphone supported by the housing. The user station may include a wireless locating sensor supported by the housing. The electrical circuitry may include computer componentry configured to transmit voice communications over a packet-switched network.

The communications port(s) may be configured for two-way communication with the patient-nurse communication system, and the user station may include a control activatable by a user to send a notification of an event relating to the patient room to the patient-nurse communication system.

In another embodiment, a user station for a patient-nurse communication system installable in a healthcare facility having a plurality of locational areas includes a housing defining an interior region. The housing is positionable adjacent a patient location of the healthcare facility. The user station also includes a communications port coupled to the housing. The communications port is configured to connect the user station to the patient-nurse communication system. The user station also includes a graphical display supported by the housing, and a memory in the housing comprising first computer program logic and second computer program logic. The first computer program logic is configured to associate the user station with a first locational area comprising at least one patient location within a healthcare facility, determine whether calls received from the patient-nurse communication system relate to the first locational area, and format information relating to calls that relate to the first locational area for display on the graphical display. The second computer program logic is configured to associate the user station with a second locational area comprising at least one patient location and spaced from the first locational area within the healthcare facility, determine whether calls from the patient-nurse communication system relate to the second locational area, and format information relating to calls that relate to the second locational area for display on the graphical display. The user station also includes electrical circuitry in the housing operable to execute the first computer program logic and the second computer program logic to enable a user to process and manage at the user station calls from the patient-nurse communication system that relate to first and second locational areas.

The graphical display may include a first window and a second window spaced from the first window, where the first window is configured to display the information relating to calls that relate to the first locational area and the second window is configured to display the information relating to calls that relate to the second locational area.

The second locational area of the healthcare facility may have at least one sub-area including a patient location and the second window of the graphical display may be configured to display information relating to calls that relate to a sub-area of the second locational area.

In another embodiment, a user station for a patient-nurse communication system includes a housing defining an interior region, a graphical display supported by the housing, electrical circuitry in the interior region and configured to send and receive signals relating to calls communicated by a patient-nurse communication system and display information relating to the calls on the graphical display, and a mounting apparatus configured to selectively mount the housing to a structure adjacent a patient location in a plurality of different mounting arrangements.

Patentable subject matter may include one or more features or combinations of features shown or described anywhere in this disclosure including the written description, drawings, and claims.

BRIEF DESCRIPTION OF THE DRAWINGS

The detailed description refers to the following figures in which:

FIG. 9 is a perspective view of a user station including a front face, a graphical touch display supported by the front face, a microphone, first and second laterally spaced sides, each including a speaker grille; a top side, a bottom side longitudinally spaced from the top side, and a code call lever adjacent the top side;

FIG. 10 is a front elevational view of a graphical touch display for a user station, including a tabular listing of calls, a scroll bar, a plurality of functional tabs, a plurality of buttons, and a plurality of icons;

DETAILED DESCRIPTION OF THE DRAWINGS

Aspects of the present invention are described with reference to certain illustrative embodiments shown in the accompanying drawings and described herein.

In general, a healthcare communication system includes one or more staff or nursing computers or computing devices, which may be referred to as stations or consoles. The stations or consoles, in cooperation with various computers, networks, and supporting equipment and services, enable nurses and other staff to receive, view, manage, and route, output or respond to electrical and wireless signals from a variety of communication, call, monitoring, detecting and/or signaling devices. Some communication, call, monitoring, detecting and/or signaling devices are operated by patients, staff, or visitors. Others are activated by the occurrence of an event or condition detected by signal receivers, patient monitoring equipment or hospital beds located throughout a healthcare facility. When the system receives a signal from a communication, call, monitoring, detecting and/or signaling device, one or more indicator assemblies may be activated to alert hospital staff of the condition or event being signaled by the communication, call, monitoring, detecting and/or signaling device.

Figure 1:
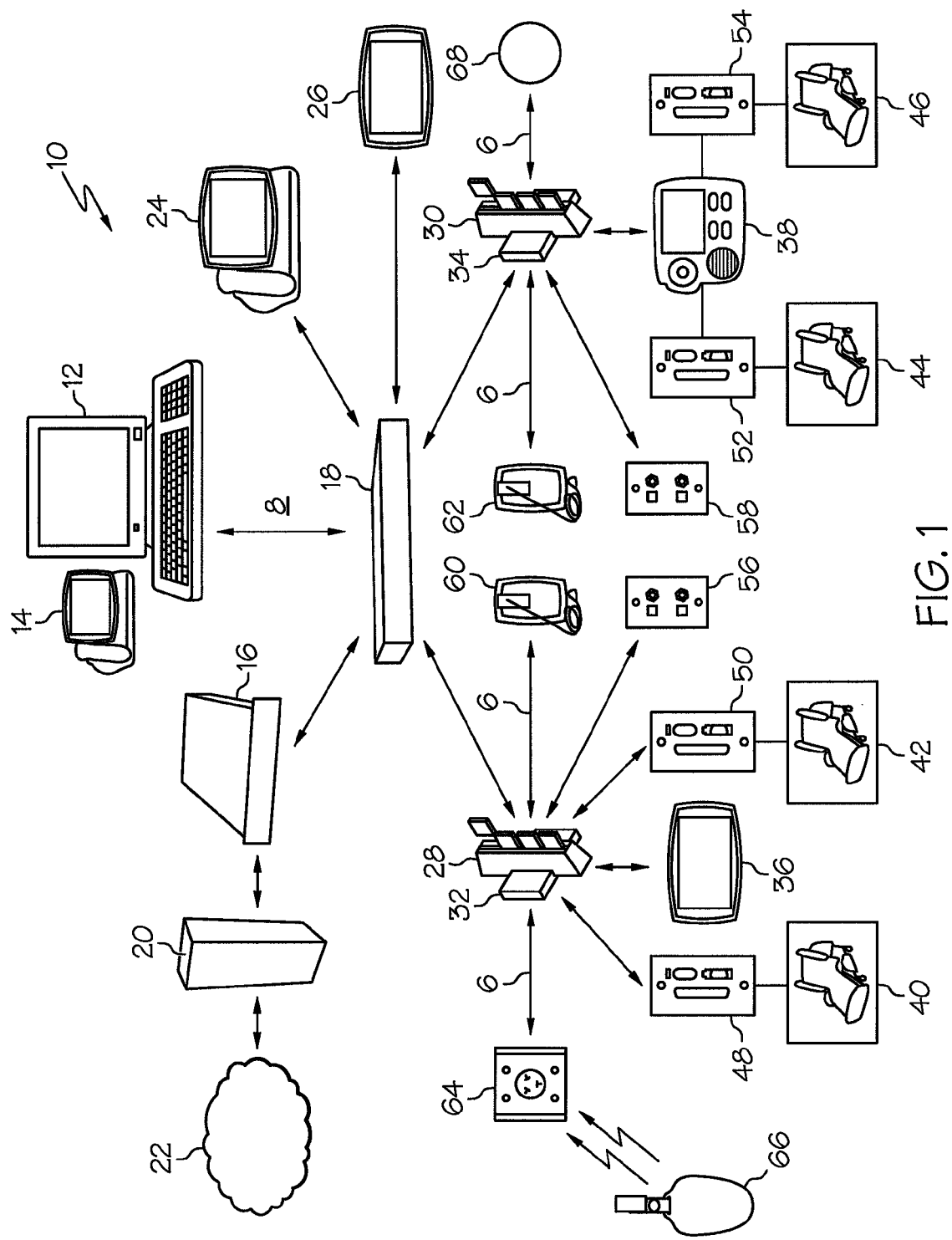
FIG. 1 is a simplified schematic showing a logical architecture for a patient-nurse communication system in communication with other components of the system.

One embodiment of a patient-nurse communication system 10 is diagrammatically illustrated in FIG. 1. System 10 includes a primary user console or station 12, a primary user console or station 14, and one or more secondary user consoles or stations 24, 26, 36, 38 which are configured to be operated by nurses or other staff. Primary station 12 enables nurses or staff to monitor activity and communicate with patients and other staff within the facility or portion of the facility monitored by the system. Primary station 12 is a computer or computing device that has a display screen, voice communication capabilities, and one or more input devices (such as a keyboard, touchscreen, mouse, switch, button, knob, or the like) configured to control the operation of the patient-nurse communication system. Voice communication capabilities are provided by an integrated microphone and speaker and/or a telephone handset.

Primary console or stations 12 and primary station 14 are configured to enable a nurse or other staff to place calls, cancel calls, monitor the location of other staff members, process calls and alerts and route or relay calls or alerts to and from other consoles or other components of the system. Primary console 12 may further be configured to enable an authorized user to update the status of calls, alerts, monitored persons and/or monitored devices or equipment, and enable or disable calls or alerts. Primary station 14 is configured to be desk-mounted but could also be wall-mounted.

Secondary user consoles or stations 24, 26, 36, 38 have similar components and provide similar but often more limited capabilities than the primary console 12 and/or the primary station 14. For example, primary console 12 may include a larger display screen, a graphical user interface configured for data entry, monitoring, and analysis, a network interface (e.g., for TCP/IP connectivity), and/or a telephone handset. However, different configurations of secondary consoles 24, 26, 36, 38 exist that may or may not have a graphical display or telephone handset, or may have limited network connectivity.

For example, console 24 has structural components that are similar to console 14 but generally does not have all the same functional capabilities as console 14 because console 24 is a secondary console. Console 24 may be configured to display only a subset of the information that is available at console 14 (i.e., console 24 may be configured to display only calls pertaining to a particular grouping of patient rooms assigned to a specific nurse, while console 14 is configured to display all call information for all rooms in a nursing unit, group of units or entire facility). Consoles 26, 36 have similar structural components and functional capabilities as console 24 but do not have a telephone handset. Console 38 is a scaled-down and potentially lower cost version of console 24, and as such has more limited graphic capabilities and restricted network connectivity.

Notwithstanding the above description, secondary consoles 24, 26, 36, 38 may have all of the components and functional capabilities as primary console. For example, a console or station may be a primary console for one nursing unit, zone or portion of a facility and also be configured as a secondary console for another unit, zone or portion of the facility. In this way, information for multiple units, zones or portions of a facility may be monitored from one station or console.

Consoles 12, 14, 24, 36, 38 are connected either directly or indirectly (i.e., through an electrical assembly, such as an input-output board) to a switch 18. In the illustrated embodiment, switch 18 is a Power over Ethernet (POE) switch, however, other suitable types of switches may be used, as will be understood by those skilled in the art. Switch 18 and electrical assemblies or input-output boards 32, 34 provide connectivity to a variety of call, communication, monitoring, detecting and/or signaling devices 40, 42, 44, 46, 48, 50, 52, 54, 56, 58, 60, 62, 64, 66, 68 to receive call and/or alert signals therefrom. Switch 18 may also be configured to provide electrical power to remote devices, as is the case with POE switches.

In general, "console" or "station" is used herein to refer to a computer or computing device configured to provide an interface to the system for a user, such as a nurse, staff member, patient, or visitor. As such, this equipment generally includes at least one output device, such as a visual display or speaker, to notify or communicate calls and/or other information to the user. Stations or consoles may also include at least one input device, such as a touchscreen, keypad or keyboard, microphone, telephone handset, push button, switch, dial, lever, or the like, to enable the user to place and/or respond to the calls or other information. Stations or consoles also include circuitry to connect them to the system 10. Stations or consoles include embodiments that may be desk- or table-mounted, as well as embodiments that may be mounted to a wall, headwall, column, bed, siderail, or other structure.

Input/output boards 32, 34 are circuit board assemblies that provide computing processing and wiring for a patient location in the healthcare facility, such as a patient room. Among other things, the electrical assemblies or I/O boards operate to convert device-specific protocols from a variety of devices, which may be installed in patient rooms, to a single network protocol suitable for communication over a network. For example, I/O boards 32, 34 convert serial links to primary and secondary consoles, remote locating receiver or bed interface unit room bus protocols, and serial to dome light protocols, on the one side, to XML-over-TCP/IP on the other side. In the illustrated embodiments, each I/O board 32, 34 includes a multimedia microprocessor with built-in multimedia capability, such as the Freescale IMX 27. Input-output boards 32, 34 may also include one or more POE ports to enable devices to connect directly to the board instead of connecting to the system through a switch.

Indicator assemblies 28, 30 are coupled to electrical assemblies or input-output boards 32, 34 and receive control signals therefrom to activate a visual or audible notification, or a combination of visual and audible notifications, at the indicator assembly.

In general, primary console 12 is in communication with electrical assemblies or input-output boards 32, 34 through a computer network 8 and switch 18. Secondary consoles 24, 26, 36, 38 are in communication with primary console 12 over network 8 through a switch 18 and may thereby receive information and commands from primary console 12. In the illustrated embodiment, network 8 is a TCP/IP network running an XML data protocol configured to enable communication among a number of devices and/or systems usable by the healthcare facility.

Call, communication, monitoring, detecting and/or signaling devices include, for example: beds 40, 42, 44, 46 (such as Hill-Rom TotalCare® or VersaCare® beds), which are linked to system 10 via bed interface units 48, 50, audio station bed connectors (ASBCs) 52, 54, or similar bed connector devices; patient monitors and other medical or clinical devices or equipment (such as therapy equipment, heart rate or respiration monitoring devices, and the like), which are linked to system 10 via connectors 56, 58; call cords 60, 62; wireless (i.e. infrared or radio frequency) location tracking receivers or "remote location receivers" 64 and related location tracking badges or tags 66, and smoke alarm 68. Some call, communication, monitoring, detecting and/or signaling devices, such as remote receiver 64, cords 60, 62, smoke alarm 68 and bed interface units 48, 50, are coupled directly to I/O boards 32, 34 by communication links 6. Other devices are coupled to I/O boards 32, 34 indirectly through consoles or stations, such as ASBCs 52, 54, which connect beds 44, 46 to station 38. In the illustrated embodiment, links 6 are RS485 connections.

For ease of description, this disclosure may use "incoming call" or "call" to refer to one or more calls, messages, communications or signals sent from a call, communication, detecting, monitoring, and/or signaling device to system 10, and may use "outgoing notification", or "notification" to refer to one or more calls, messages, communications, alarm signals, alert signals or other indications or annunciations that are configured to notify or otherwise direct the attention of a nurse or other staff member of, or associated with, the facility to an incoming call. Further, this disclosure may use "call device" to refer individually or collectively to such call, communication, detecting, monitoring, and/or signaling devices.

As shown in FIG. 1, switch 18 links various components of system 10 to a primary station 12, 14. Primary console or station 12, 14, alone or in combination with one or more other server computers and/or computing devices, hosts and executes software and services needed to operate system 10. Primary station 14 is configured to process control messages generated by system 10 and send them to the appropriate destination or endpoint, such as a secondary console, I/O board, or other electrical assembly. As such, primary station 14 includes a soft telephony switch and related componentry.

Primary station 14 is configured to operate and manage many of the primary nurse call functions of system 10, such as receiving and managing messages from various connected devices, synchronizing devices that come online, controlling placement and canceling of calls, answering of calls, generating of notifications or alerts, acknowledging and canceling of notifications and alerts, managing location information for staff and devices, activating and deactivating staff, managing staff-patient assignments, assigning and managing roles and responsibilities to staff and devices, and managing patient information and patient discharges and transfers.

Switch 18 may also link system 10 to an "enterprise" server 16. Enterprise server 16 may be configured to enable system 10 to interface with systems or services that are considered "external" or "optional" to system 10. For example, server 16 may be coupled to a telecommunications server 20, which acts as a gateway to a facility's telecommunications infrastructure 22. Infrastructure 22 generally includes a network that is configured to facilitate communication among a variety of telecommunication devices, including analog and digital devices, fixed telephones and mobile or cellular devices, personal digital assistants (PDAs), pagers and the like. For example, infrastructure 22 may include a public switched telephone network (PSTN) or private branch exchange (PBX) or the like.

Figure 2:
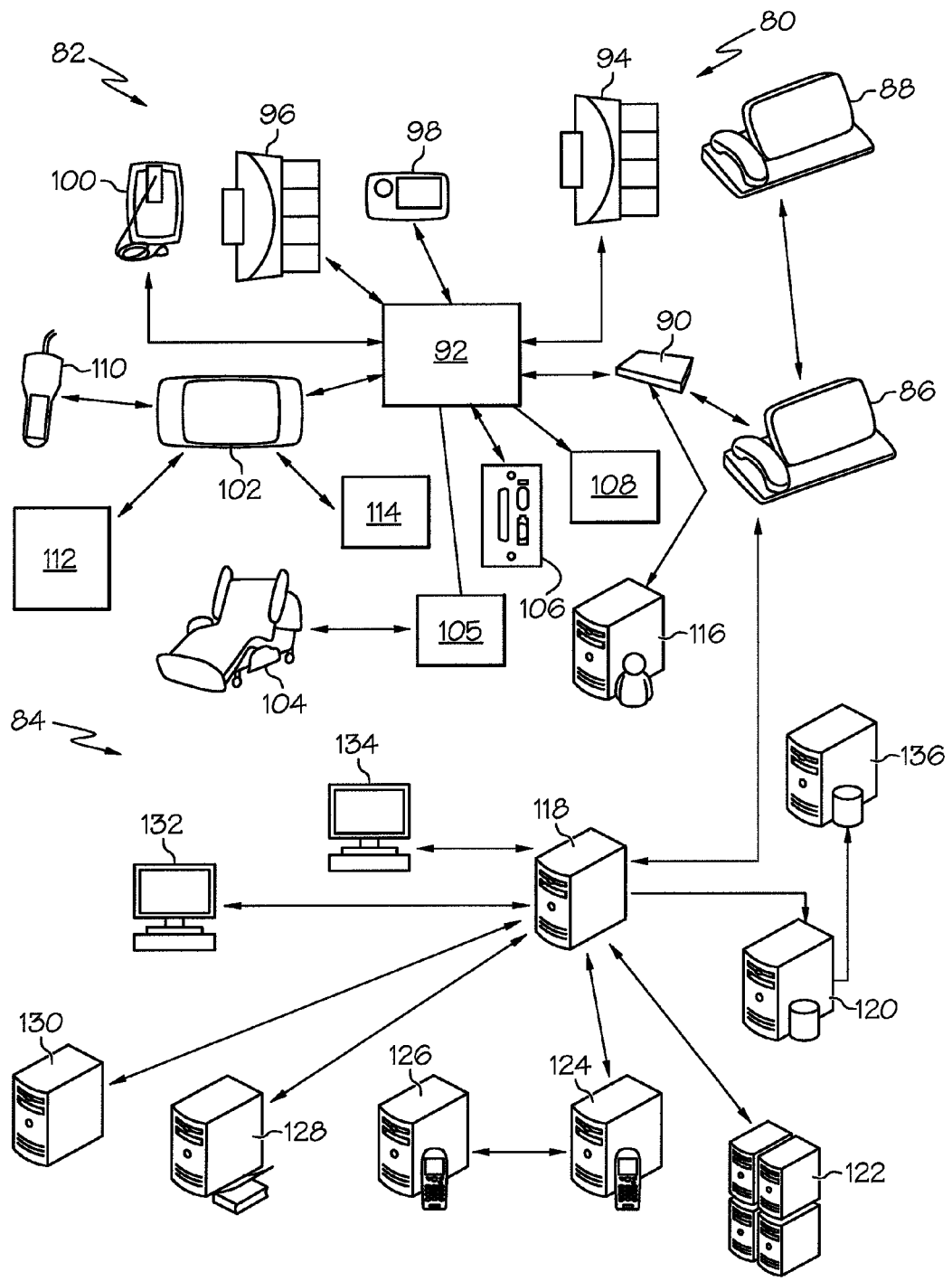
FIG. 2 is a simplified schematic showing physical components of a patient-nurse communication system showing connectivity to other services and systems.

FIG. 2 illustrates connectivity among components of an embodiment of a healthcare communication system 80 including a nurse call system 82 and a plurality of other services and/or systems 84. Nurse call system 82 includes a primary console 86 operably coupled to a switch 90, and a secondary console or station 88 logically coupled to primary console 86 and physically coupled to switch 90. Secondary console 88 is configured to display information about a nursing unit or units for which it is not the primary console.

Switch 90 is operably coupled to I/O board 92 and server 116. I/O board 92 is configured to receive incoming calls from a variety of devices connected thereto, including but not limited to indicator assemblies 94, 96, secondary console 98, call cord or switch 100, secondary console 102, bed 104, bed interface unit 106, remote locating receiver 108, and pillow speaker 110. In general, these devices are connected to I/O board 92 by an RS 485 link. Additional devices, such as bed connector 112 and call cord 114, may be coupled to or integrated with a secondary console such as console 102 and thereby connected to system 80. One embodiment of an electrical assembly or I/O board is IBM Part No. 43T2063.

An interface 105 is operable to connect bed 104 to I/O board 92. In the illustrated embodiment, interface 105 is a 37 pin connector (not shown) facing outward that a bed plugs into. On the other side of the interface 105, wires are connected to each pin of the 37 pin connector (not shown) that could be run to other devices that the bed controls, such as lighting controller, TV, radio, and nurse call patient stations. It may be used in place of a bed interface unit or ASBC.

Server 116 is a VOIP server configured to translate system operations and communications to the corresponding messages that then control endpoint devices, such as nurse or staff stations, consoles or room input/output boards. As such, server 116 includes a soft telephony switch and other associated componentry. Server 116 may also provide integration with the hospital telecommunications structure (e.g., PBX or other voice communication system). In the illustrated embodiment, server 116 is a Windows server running 3CX.

Primary console 86 may optionally be coupled to a second server 118 by a network 115, such as a TCP/IP network. Server 118 may also be coupled to switch 90. Server 118 is similar to enterprise server 16 described above.

Other services and components of system 84 are in communication with network 115 through server 118. Such other services or components may include a database server 120, one or more third party servers 122, a first wireless communications server 124 for managing communications to and from wireless telecommunications devices, a second wireless communications server 126 for handling communications to and from wireless badges for locating and tracking of staff members, a user authentication server 128 for managing user accounts, passwords, and user authorization; a third party product integration server 130, which facilitates integration with third party or legacy products or services; a hospital administrative client 132 for conducting administrative tasks relating to patients and staff, such as adding patients and assigning staff to patients; and a status or reports server 134 for managing displays and reports of calls and notifications for one or more locations in the facility.

While the term "server" is used herein, it will be understood by those skilled in the art that the functionality represented or performed by these elements may comprise software programs or services that may be resident and/or executable by any computer, device or equipment in the system or more than one computer, device or equipment in the network.

In the illustrated embodiment, server 124 is configured to provide communication and configuration for wireless devices using Emergin Wireless Office; server 126 is configured to provide communication and configuration for wireless Vocera devices; server 130 is configured to interface with a Hill-Rom NaviCare system to receive and process alerts therefrom; and server 134 is configured to operate an "electronic status board," which displays locations within the facility and current information about them, such as active calls, bed status information, staff located in the location, and staff assigned to the location.

Figure 3:
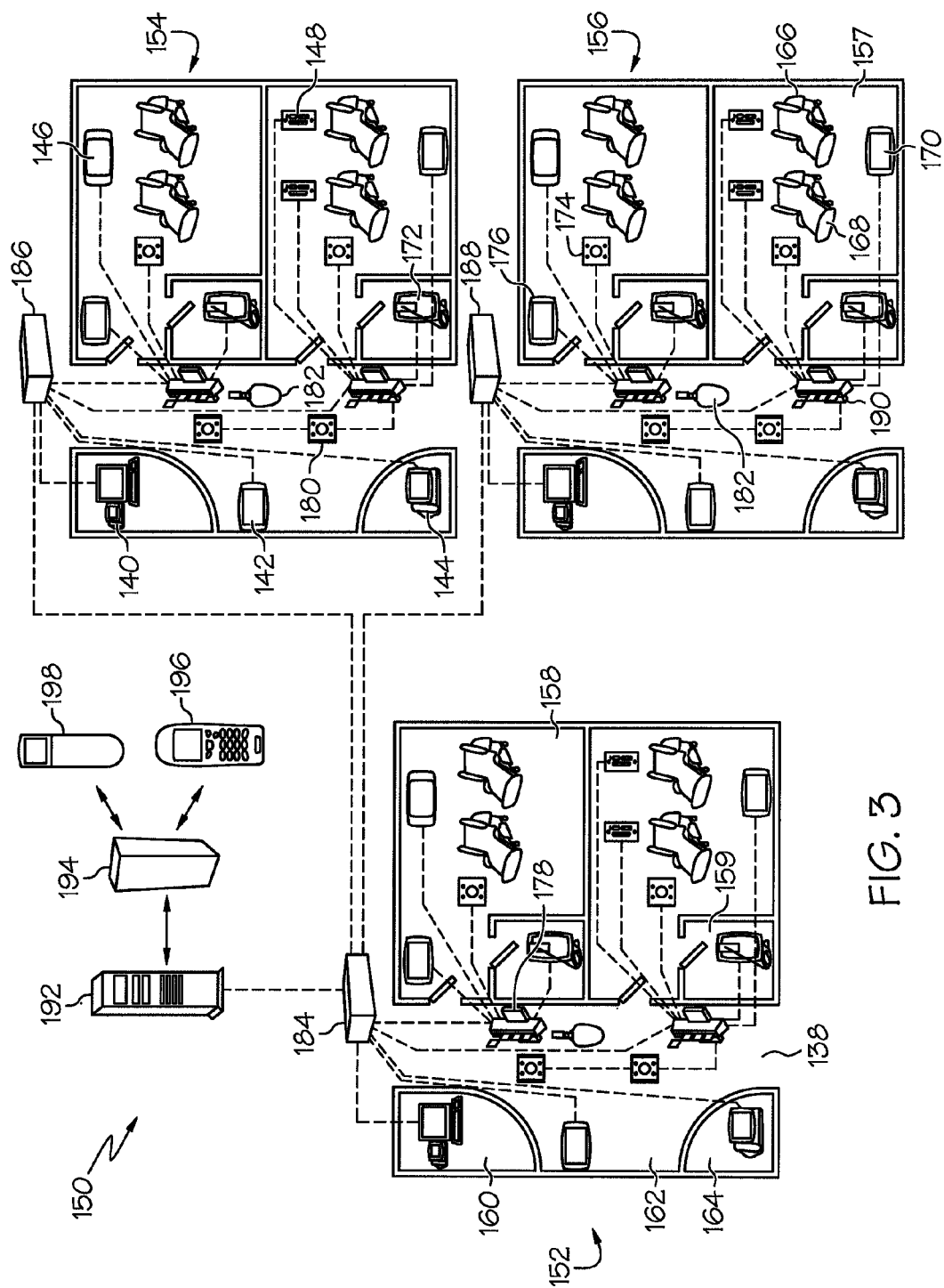
FIG. 3 is a simplified diagrammatic view of an exemplary implementation of a patient-nurse communication system in a patient care facility.

FIG. 3 diagrammatically shows an illustrative implementation in a facility of a healthcare communication system 150 including many of the components described above. The illustrated facility has a plurality of nursing units or zones 152, 154, 156, each of which has one or more patient rooms or locations 158, hallways or common areas 138, and staff locations 160, 164. Each patient room 158 has a bathroom or washroom 159.

A number of call monitoring and/or communication or signaling devices are located throughout the facility, including primary consoles 140, secondary consoles 142, 144, 146, 170, 176, bed interface units 148 and beds 166, 168, toilet, bath and/or shower switches 172, wireless locating receivers 174, 180, and wireless locating transmitter badges 182. In the illustrated configuration, each nursing unit 152, 154, 156 includes a primary console 140, and each patient room includes at least one secondary console 146 and at least one switch 172 located in the bath/washroom 148.

An indicator assembly 190 is mounted in the hallway 138 outside of each patient room 158. Indicator assemblies 190 may be mounted either to a wall or ceiling, above the door to the room or in another suitable location indicative of the patient room with which the indicator assembly is associated. An electrical assembly or I/O board 178 is also associated with each patient room and may be mounted adjacent to each indicator assembly. Additional details regarding indicator assemblies of the type referred to herein may be found in U.S. Provisional Patent Application entitled INDICATOR ASSEMBLY FOR HEALTHCARE COMMUNICATION SYSTEM, application Ser. No. 61/066,883, filed on Feb. 22, 2008, which is incorporated herein by reference.

Secondary consoles 142, 144 may also be located in hallways 138 and staff locations 160, 164. Locating and tracking receivers 174, 180 are provided in the patient rooms 158, hallways 138 and other locations.

A POE switch 184, 186, 188 is associated with each unit 152, 154, 156 and operably coupled to the devices of its respective unit. System server 192 is coupled to switch 184, which is in turn coupled to switches 186, 188 in the illustrated embodiment. System server 192 is similar to server 118 described above. VOIP server 194 is operably coupled to server 192 and to telecommunications devices 196, 198, substantially as described above.

In operation, when a call or signal is initiated by one of the call initiating devices, executable computer logic processes the call or signal, determines which nurse or staff member to notify of the call, if a notification is necessary, locates the nurse or staff member, and routes an appropriate notification or notifications to one or more output devices associated with the assigned nurse or staff member or within the closest proximity to the assigned nurse or staff member. At the same time, a notification is routed to the output device nearest the location where the call originated. Such computer logic may be located in memory at a primary console, I/O board or at the application server 192.

For example, if a nurse is assigned to units 152 and 156, is currently tending to a patient in room 157 of unit 156, and a patient or piece of monitoring equipment in room 158 issues a call, then system 150 locates the nurse using room receivers 174 and hall receivers 180 and the nurse's badge 182. System 150 then activates the appropriate visual and/or audible notifications at the indicator assembly 178 assigned to the patient room where the call originated. System 150 may activate a visual and/or audible notification at the console 170, nearest the nurse's location, as well. System 150 may cancel or disable one or more of the notifications when the locating receivers detect that the nurse has departed the area or when the nurse enters the room 158 where the call originated.

Additional details describing the structural components, connectivity, functionality, and other operations of the above-described communication systems may be found in U.S. Provisional Patent Application entitled DISTRIBUTED HEALTHCARE COMMUNICATION SYSTEM, application Ser. No. 61/066,877, and U.S. Provisional Patent Application entitled DISTRIBUTED FAULT TOLERANT ARCHITECTURE FOR A HEALTHCARE COMMUNICATION SYSTEM, application Ser. No. 61/066,918, both of which were filed on Feb. 22, 2008 and are incorporated herein by reference.

Various embodiments of a user station suitable for use in a healthcare communication system such as described above and in the related applications, which are incorporated herein by reference, are shown in FIGS. 4-24 and described below.

Figure 4:
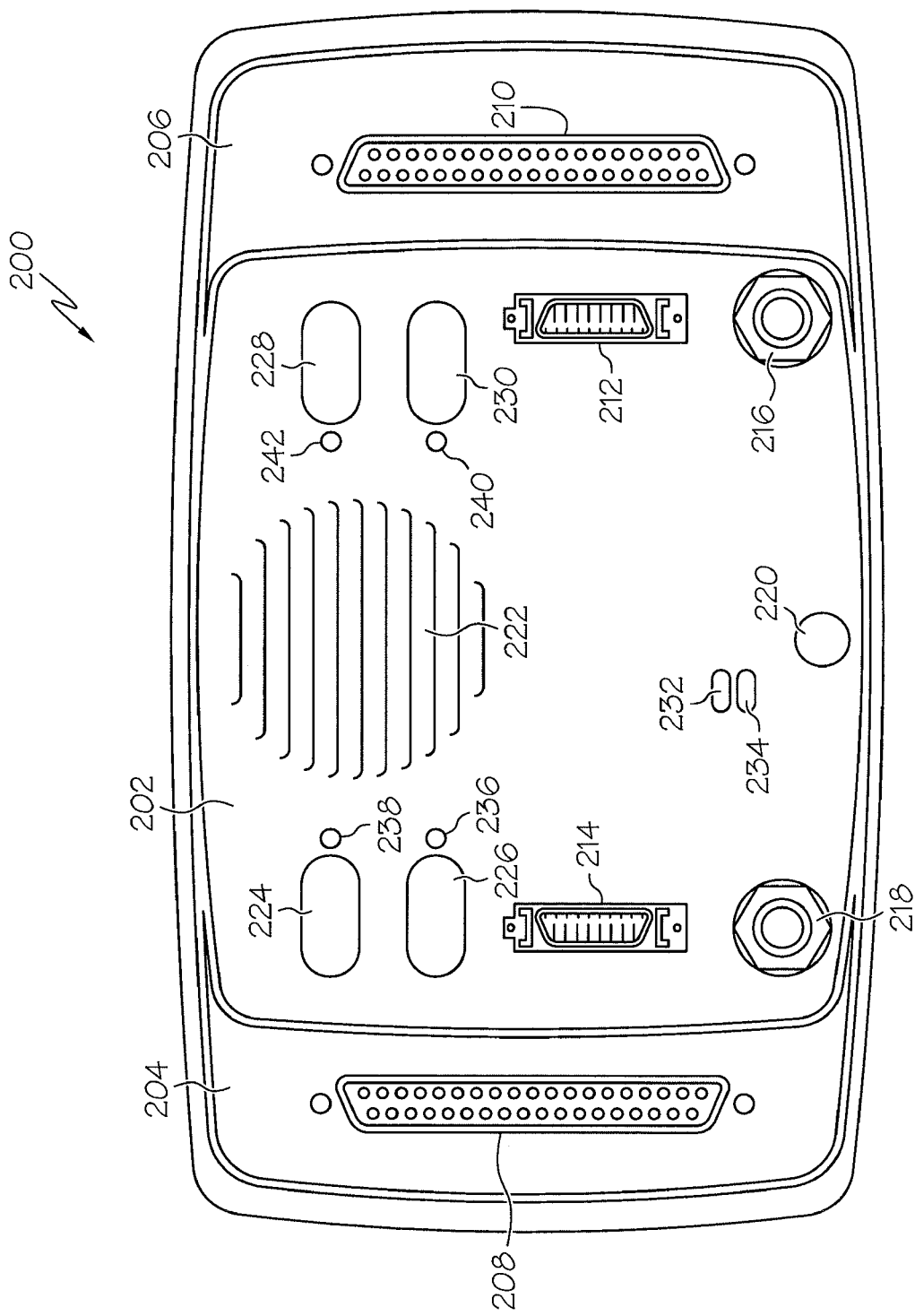
FIG. 4 is a front elevational view of a user station including a plurality of connector ports, a speaker, a microphone, a plurality of buttons and a plurality of visual indicators.

FIG. 4 is a front elevational view of a user station 200 including a plurality of connector ports 208, 210, 212, 214, 216, 218, a speaker 222, a microphone 220, a plurality of buttons 224, 226, 228, 230 and a plurality of visual indicators 232, 234, 236, 238, 240, 242. All of the aforementioned elements are located on the front face 202, which has a first side face 204 and a second side face 206 located on either side. Connectors 208, 210 are 37-pin connectors suitable for connecting user station 200 to a hospital bed system, such as Hill-Rom's TotalCare® or VersaCare® beds), or to other monitoring or therapy equipment to receive signals therefrom and convey the signals to the healthcare communication system. Connections 212, 214,216, 218 may be used to connect a pillow speaker, call cord, or other equipment or devices from which it may be desirable to receive signals to convey to the healthcare communication system. User station 200 is capable of receiving and outputting voice communications but does not have a graphical user interface.

In general, buttons 224, 226, 228, 230 are user input devices such as membrane switches or other electromechanical buttons, which enable a user to place calls of different types (e.g., normal, code blue, staff call, staff emergency, etc.) and cancel a call previously made from the station. Visual indicators 232, 234, 236, 238, 240, 242 are light emitting diodes (LEDs) that are generally lit when a particular function of the station 200 is active and unlit when the function is not active. For example, LED 232 is lit when a call has been placed, and LED 234 is lit when an audio communication line is open, allowing the user to convey voice communications through the healthcare communication system through user station 200.

Figure 5:
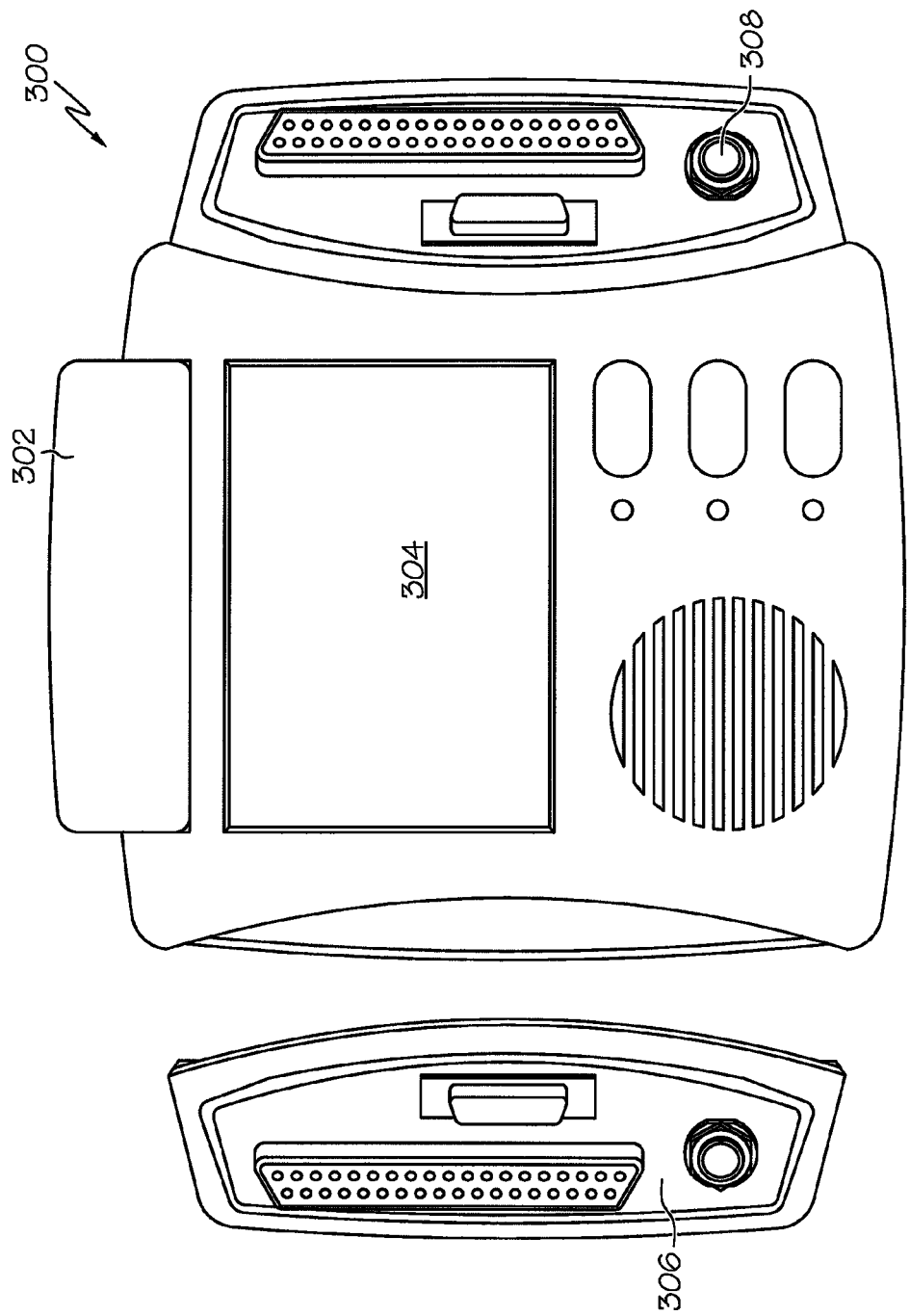
FIG. 5 is a front elevational view of a user station similar to the embodiment of FIG. 4, including removable side portions, each of which includes a plurality of connector ports; and a "code" or emergency call button.
Figure 6:
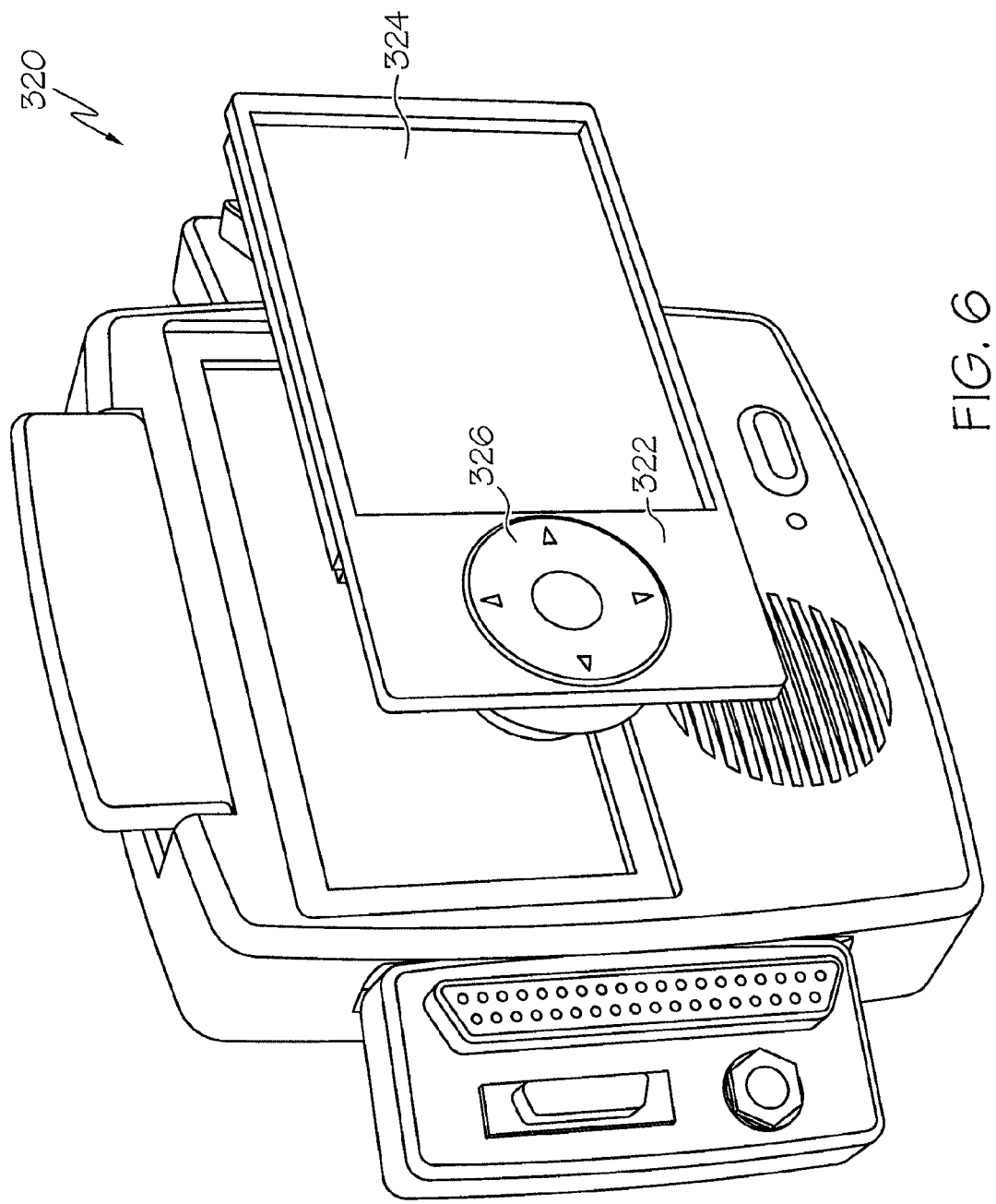
FIG. 6 is a perspective view of a user station similar to the embodiments of FIGS. 4 and 5, including a visual display portion and a multifunctional user control.

FIG. 5 is a front elevational view of a user station 300, which is similar to the embodiment of FIG. 4, including removable side portions 306, 308, each of which includes a plurality of connector ports and a "code" or emergency call button 302. However, while embodiment 200 does not have graphical user interface capabilities, embodiment 300 includes an area 304, which may be configured to support a visual display, such as a graphical user interface or LCD display 324, as shown in the embodiment 320 of FIG. 6. Visual indicator assembly 322 of FIG. 6 includes display 324 and user input device 326, which operates similarly to a computer mouse or track ball, to enable a user to select, activate or deactivate options displayed on the user interface 324. The removability of side portions 306, 308 from user station 300 provide adaptability and scalability, so that side portions 306, 308 can be removed from user station 300 in facilities where bed and/or equipment monitoring features are not needed or desired, potentially resulting in a cost savings to the facility.

Figure 7:
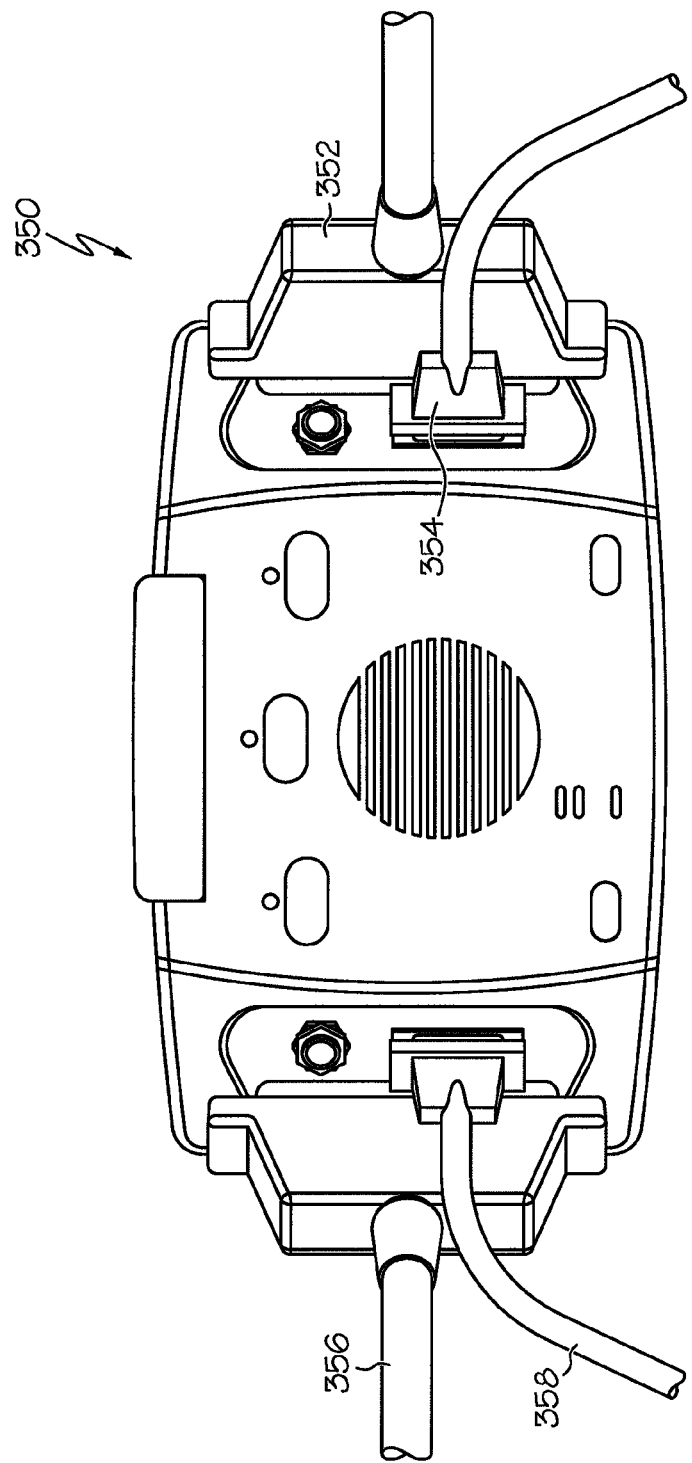
FIG. 7 is a front elevational view of a user station similar to the embodiments of FIGS. 4 and 5, showing a plurality of connectors connected to the connector ports.

As noted above, FIG. 6 is a perspective view of a user station 320 similar to the embodiments of FIGS. 4 and 5, including a visual display portion 324 and a multifunctional user control 326. FIG. 7 is a front elevational view of a user station 350 similar to the embodiments of FIGS. 4 and 5, showing a plurality of connectors 352, 354, 356, 358 connected to the connector ports.

Figure 8:
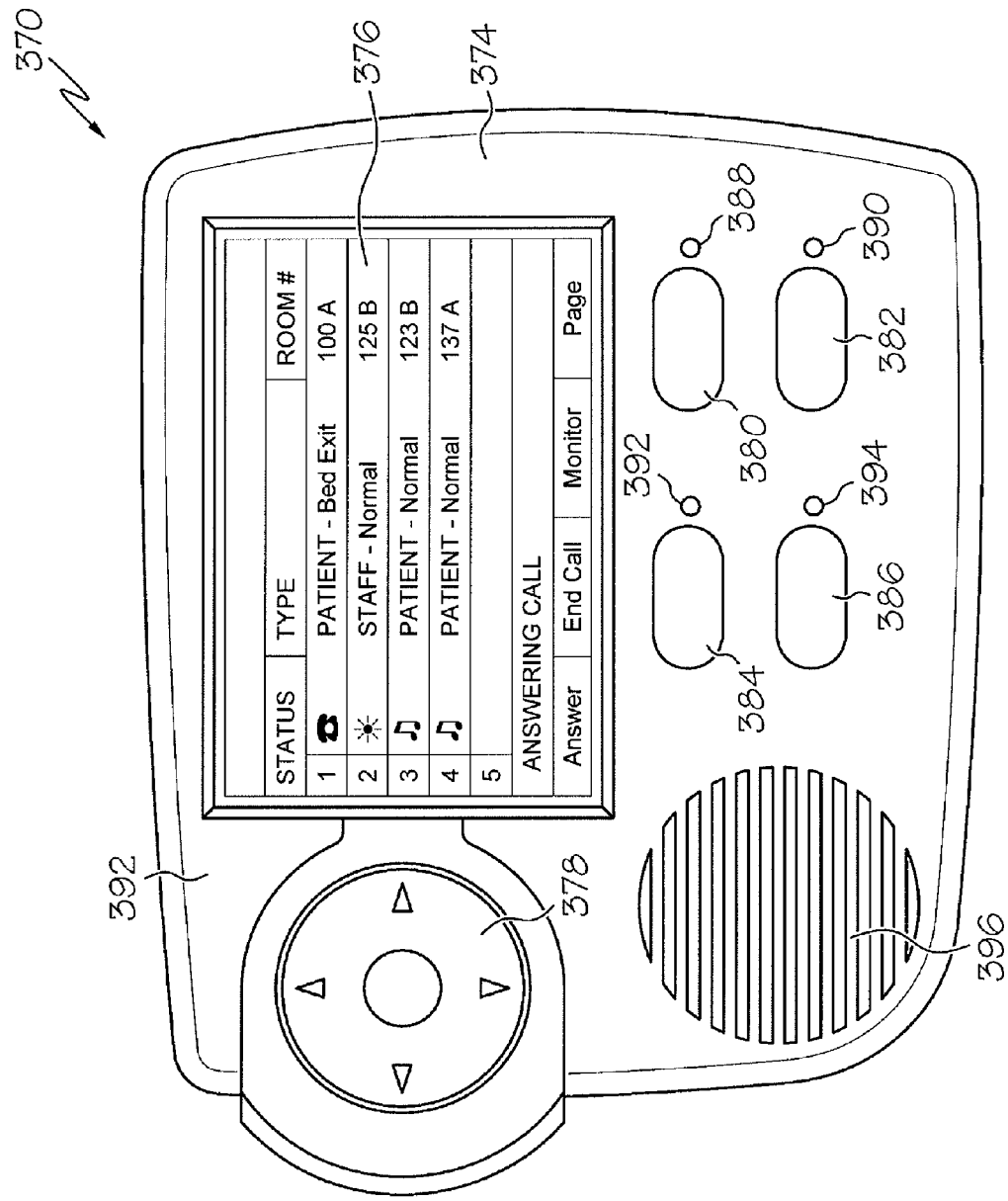
FIG. 8 is a front elevational view of a user station including a graphical display supported by the front face, a plurality of user controls, a plurality of visual indicators, and a speaker.

FIG. 8 is as front elevational view of a user station 370 including a housing 374 having a front face 372, a graphical display 376 supported by the front face 372, a plurality of user controls 380, 382, 384, 386 usable to place or cancel calls to the healthcare communication system, a plurality of visual indicators (LEDs) 388, 390, 392, 394, a speaker 396 and a user input device 378. Graphical display 376 is generally an LCD display but does not have touch input capability; hence, user input device 378 is configured to enable a user to scroll through the call list and activate or deactivate the features of the display 376 (such as answer call, end call, monitor calls, and page a staff member), much like a computer mouse or track ball-type device.

FIG. 9 is a perspective view of a user station 400 having a housing 402 including a front face 404, laterally spaced sides 406, 410, a top side 408 and a bottom side 412 longitudinally spaced from the top side 408. Station 400 includes a graphical touch display 416 supported by the front face 404, and a microphone 426. First and second laterally spaced sides 406, 410 each include a speaker grille 424. A code call lever 428 is provided adjacent the top side 408. Station 400 is typically installable in patient rooms, near the headwalls, for example. As such, it is configured to be mountable to a wall, headwall, architectural wall unit or other substantially vertical structure. Another embodiment similar to station 400 is shown in FIGS. 34-37 of U.S. Provisional Patent Application Ser. No. 61/066, 882, filed Feb. 22, 2008. FIGS. 34-35 of such provisional application show a user station including a microphone and call placed indicator supported by the front face, while FIGS. 36-37 of such provisional application show connector ports on the rear face and connectors connected thereto.

Station 400 may also be used as a staff or duty station to place and receive calls from areas normally reserved for staff members. As such, computer program logic or software is executed to configure station 400 for use by a patient or a staff member. For instance, graphical display 416 will embody more limited functionality when configured for patient use (i.e., it will enable a patient to place calls but not to view the call list or monitor calls). The configuration of a front face housing 404 is such that display 416 and microphone 426 are in substantially the same plane as the front face housing 404, such that the entire front face including these elements is substantially smooth in appearance and structure. The absence of ridges or other nonconformities that may result from the use of pushbuttons, LEDs, and placement of speaker on the front face enables the front face to be more easily cleaned. The use of touch sensors or actuators on the display 416 eliminates the need for physical buttons and results in a smooth, cleanable surface. The side-mounted speakers make the front face easier to clean as well.

Station 400 includes a printed circuit board assembly including electrical componentry, such as a multimedia microprocessor and other related components, to enable pre-recorded audio files (e.g., .wav files) to be output by the speakers of station 400. The ability to play pre-recorded sound files offers flexibility in designing and recording sounds to meet varying needs of facilities. In one embodiment, station 400 includes two circuit boards, a main board and a daughter board mounted to the main board. The daughter board may be used to house connectors for Ethernet componentry or for other purposes. One embodiment of such a circuit board is IBM Part No. 43T2071.

The circuitry of station 400 also includes IEEE 802.3af compliant components so that station 400 can be powered by Power over Ethernet (PoE) network switches. The circuitry of station 400 also includes componentry that incorporates session initiation protocol (SIP) compliant voice over Internet protocol (VoIP) within the station itself. Station 400 also includes software executable by a processor to enable a user to select the method of contacting another user (such as voice routed to a located staff position, wireless telephone or other wireless device, or text page to a wireless device. Support for PoE reduces the number of cables connected to the station by combining power and network connectivity in one cable. IEEE 802.3af compliance provides flexibility to use a variety of network switches marketed by numerous manufacturers and thereby enhance cost competitiveness. Inherent SIP compliant VoIP provides flexibility to use a variety of private branch exchange (PBX) products marketed by numerous manufacturers and thereby enhance cost competitiveness. These aspects of station 400 may also be incorporated into other embodiments of stations described herein. They are also described in the aforementioned related patent applications, which are incorporated herein by reference. Exemplary embodiments of station 400 are IBM Part No. 43T2071 and IBM Part No. 43T2067 and IBM Part No. 43T1863.

FIG. 10 is a front elevational view of a graphical touch display 440 for a user station, including a tabular listing of calls 460, 462, a touch-activated scrolling mechanism 456, a plurality of touch-activated functional tabs 442, 444, 446, a plurality of touch-activated buttons 448, 450, 452, 454, and a plurality of icons 457, 458. Enhanced graphics capabilities are used to selectively highlight or shade certain areas of the display, for example, the first call 460 in the list is highlighted relative to the other calls in the list, and the first functional tab 442 is set off graphically from the currently inactive tabs 444, 446. Further, icons 457, 458 are set off from the rest of the display by the use of different colors. For example, the emergency icon 457 is red while the assistance icon 458 is yellow.

Figure 11:
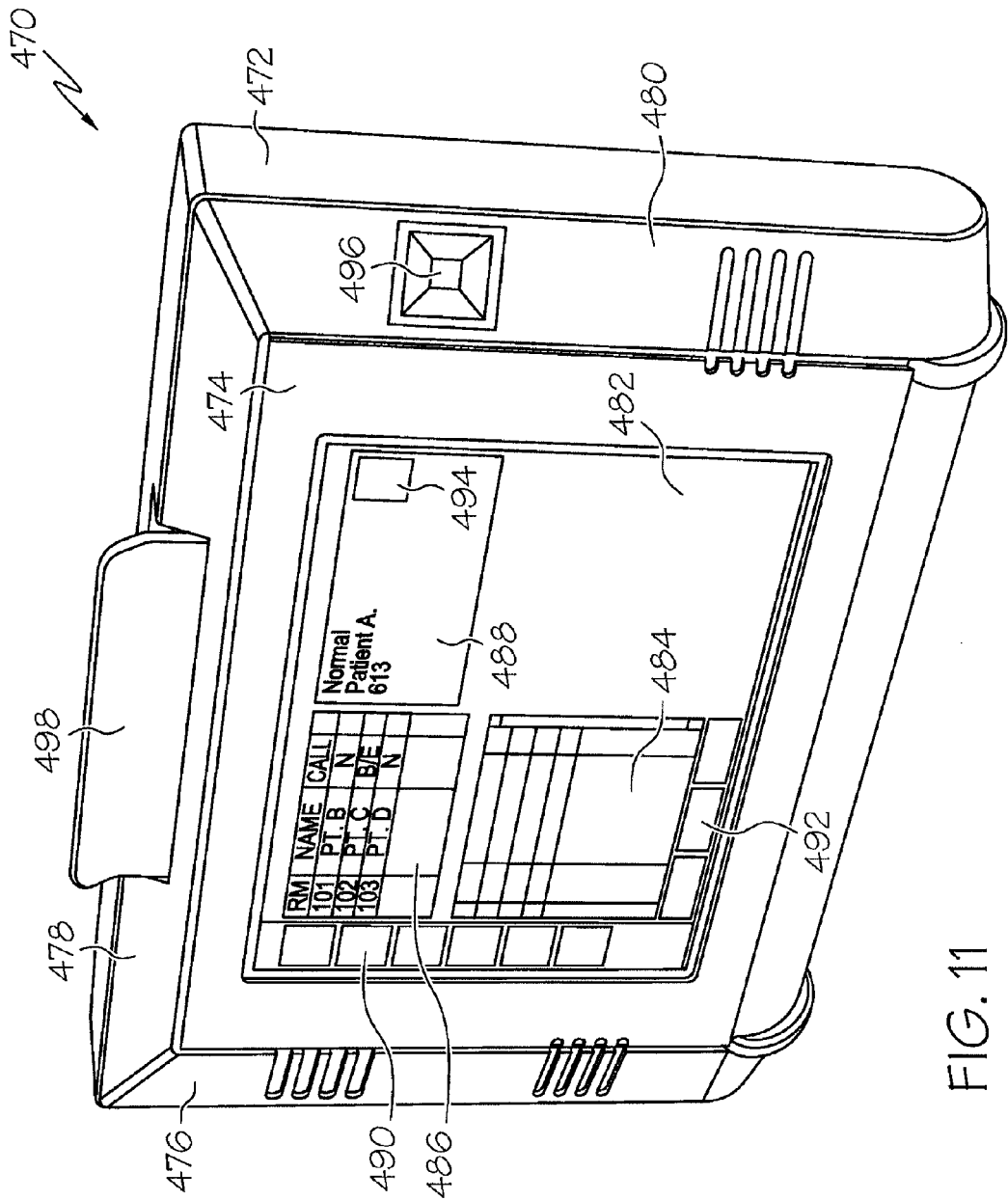
FIG. 11 is a perspective view of a user station including an enlarged graphical touch display supported by a housing having a front face, the display including a plurality of programmable windows, icons, buttons, text fonts and text lists; a top side, a bottom side longitudinally spaced from the top side, a first side, a second side laterally spaced from the first side, a code call lever coupled to the top side, and a microphone supported by the second side.

FIG. 11 is a perspective view of a user station 470 including an enlarged graphical touch display 482 supported by a housing 472 having a front face 474 and beveled sides 476, 478, 480. In the illustrated embodiment, the graphical display is about 10 inches in size. The display 482 includes a plurality of programmable windows 484, 486, 488, icons and touch activated buttons 490, 492, 494, and text fonts and text lists as shown. Station 470 has a code call lever 498 coupled to the top beveled side 478, thereby not contacting front face 474, and a microphone supported by the beveled side 480, also thereby not in contact with front face 474.

Figure 12:
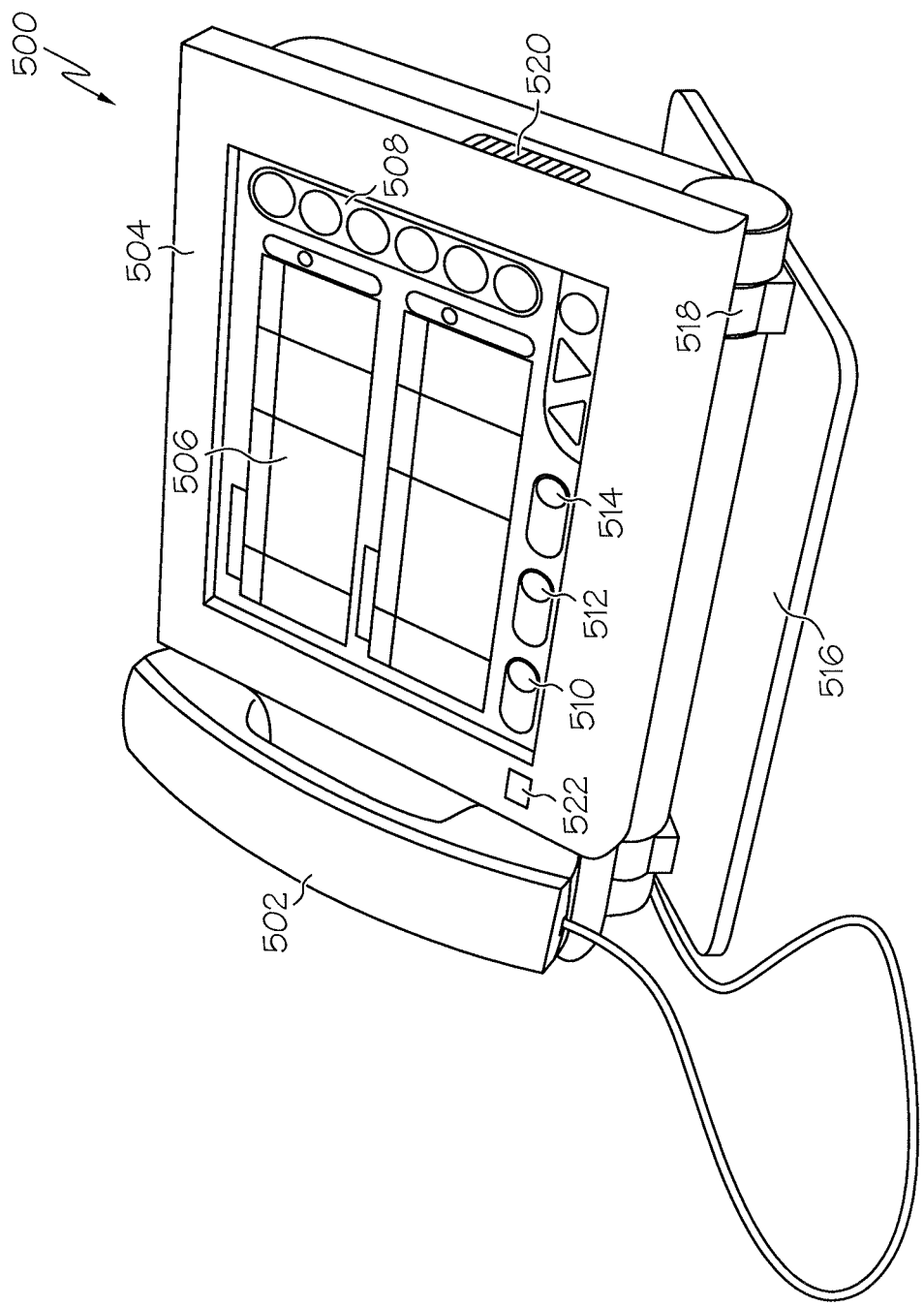
FIG. 12 is a perspective view of a user station including a housing having a front face, first and second laterally spaced sides, a top side and a bottom side longitudinally spaced from the top side, and a back side spaced from the front face, an enlarged graphical touch display with enhanced resolution supported by the front face, a microphone flush with the front face, a speaker grill located on at least one of the laterally spaced sides, a desk mount supporting the housing, and a telephone handset adjacent the front face.

FIG. 12 is a perspective view of a user station 500 including a housing having a front face 504, first and second laterally spaced sides, a top side and a bottom side longitudinally spaced from the top side, and a back side spaced from the front face. An enlarged graphical touch display 506 with enhanced resolution is supported by the front face. A microphone 522 is substantially flush with the front face, as is display 506. A speaker grill 520 is located on at least one of the laterally spaced sides. A desk mount 516 supports the station housing, and a pivot coupler 518 enables pivoting of station 500 relative to desk mount 516. A telephone handset 502 is provided adjacent the front face 504. Display 506 includes touch activated buttons and icons 508, 510, 512, 514, which are set off from each other by selective coloring, shading or highlighting as described above, for ease and efficiency of use, so that a user does not have to take time to carefully search the display for the appropriate button. A Super Video Graphics Array (SVGA) touch display, a VGA touch display, or a higher resolution touch display may be used.

FIGS. 38-42 of U.S. Provisional Patent Application Ser. No. 61/066,882 show front, side and rear perspective views of an embodiment of a desk-mountable user station similar to the embodiment of FIG. 12 and FIGS. 27-28. FIGS. 38-39 of such provisional application show the location of the microphone and call placed indicator. FIG. 40 of such provisional application shows the placement of the telephone handset relative to the user station. FIGS. 41-42 of such provisional application show the desk mounting apparitions including a pivot coupler, such as a friction hinge. FIG. 41 of such provisional application also shows a plurality of connector ports located on the back face of the user station housing.

Figure 13:
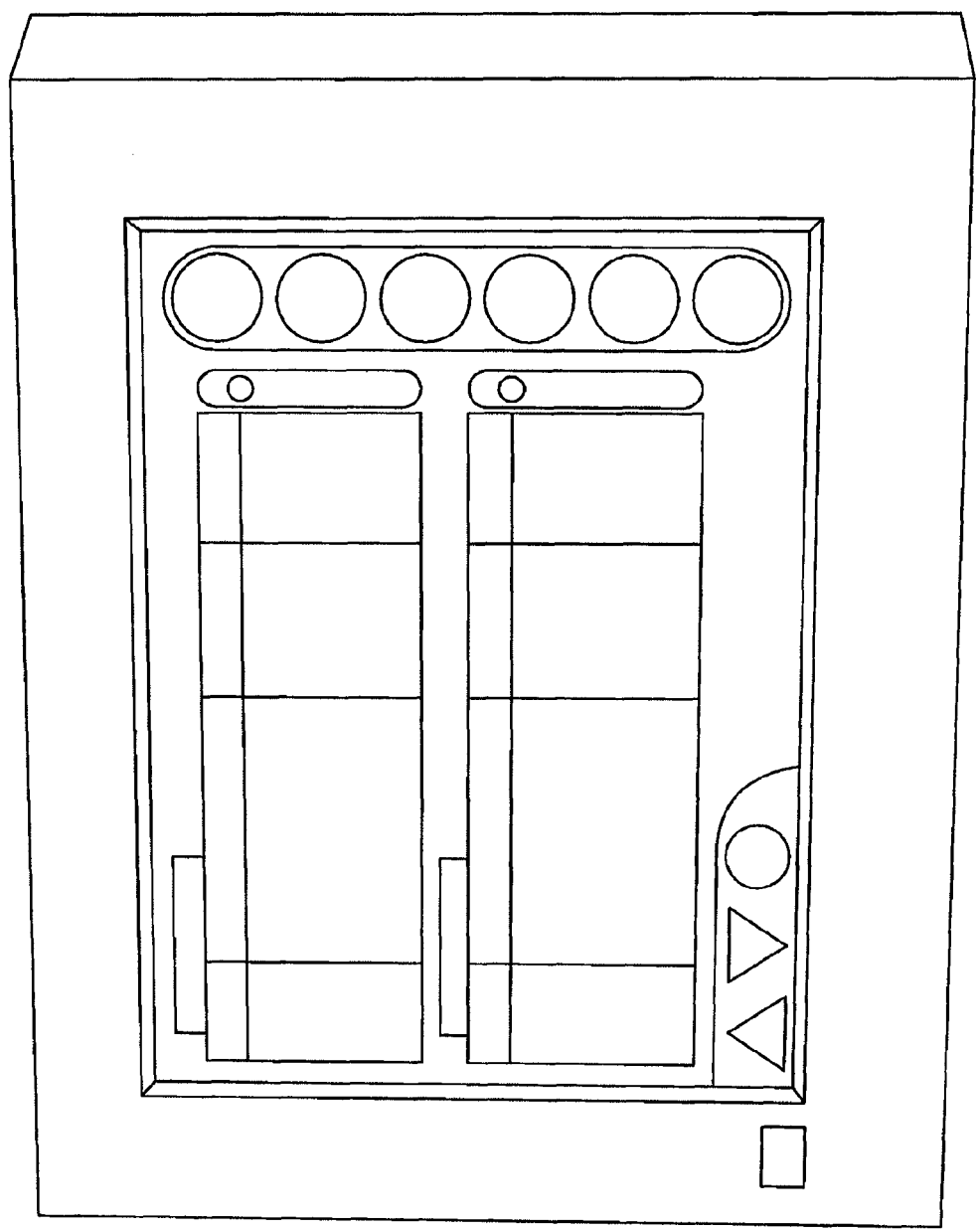
FIG. 13 is a front elevational view of a user station similar to the embodiment of FIG. 12, configured to be mounted to a wall, headwall, wall units, and other substantially vertical structures.

FIG. 13 is a front elevational view of a user station 530, which is similar to the embodiment of FIG. 12, however station 530 is configured to be mounted to a wall, headwall, wall units, and other substantially vertical structures. Exemplary embodiments of user stations 500, 530 are IBM Part No. 43T2058, IBM Part No. 43T1871, and IBM Part No. 43T1866.

Stations 470, 500 may be used as either a staff console, a staff station/annunciator, or a patient station. Computer software is executable to program or configure the graphical display to provide the functional capabilities that are appropriate for the particular selected use. In general, either of stations 470, 500 may be used as the primary user interface for nurses and other staff members to view and answer incoming calls and to communicate with patients or staff. Stations 470, 500 may also be programmed to enable users to view staff location information.

Figure 14:
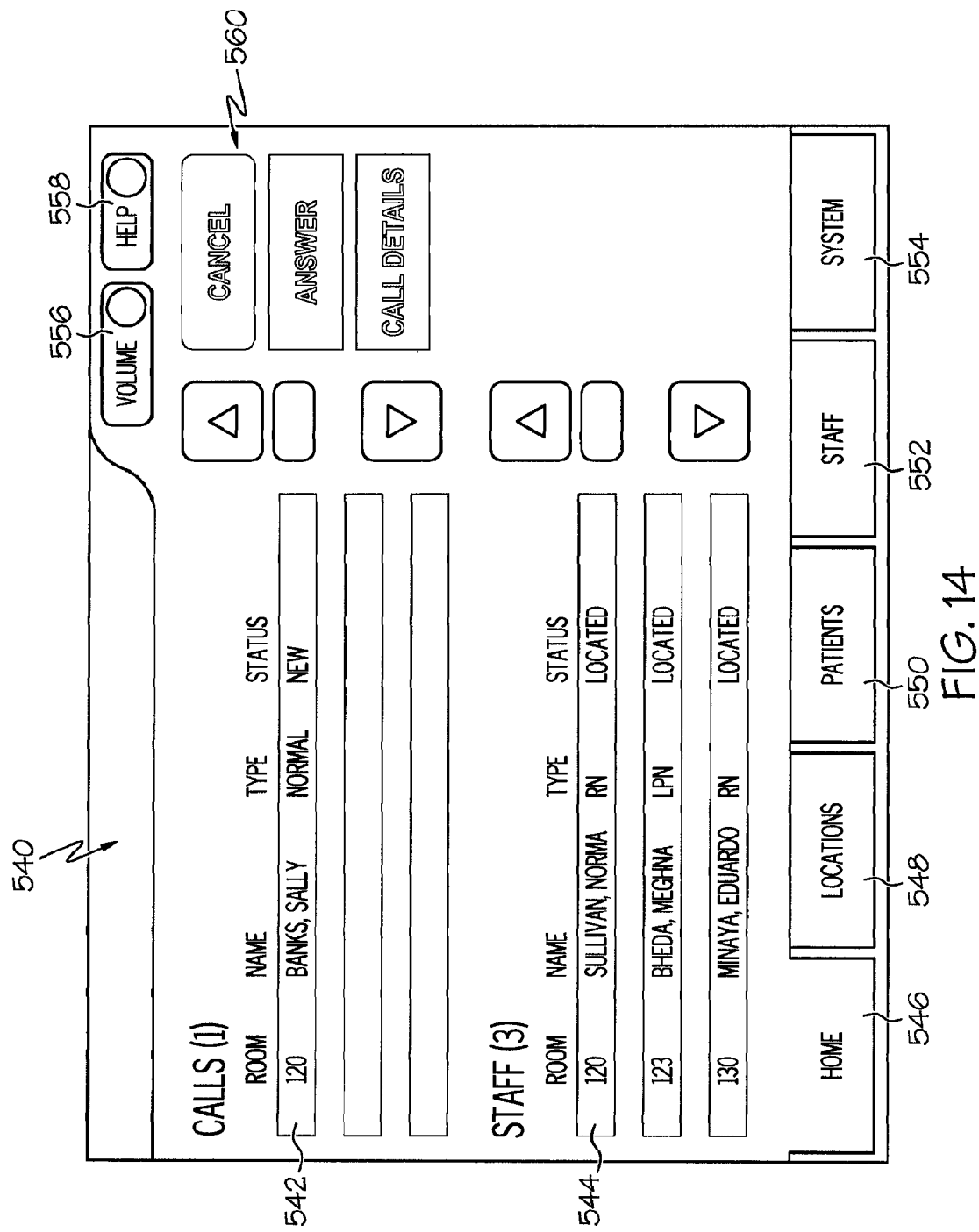
FIG. 14 is a graphical touch display for a user station, including a plurality of programmable windows, icons, buttons, text fonts and text lists; showing a first window containing a call list and a second window containing a staff list, each of the windows being scrollable, and a plurality of functional tabs and other controls that are touch-activatable.

FIG. 14 is a graphical touch display 540 for a user station, including a plurality of programmable windows, icons, buttons, text fonts and text lists. Display 540 includes a first window 542 containing a call list and a second window 544 containing a staff list. The total number of calls and located staff is displayed, as shown. Each of the windows are scrollable by a touch activated control on the display screen. A plurality of functional tabs 546, 548, 550, 552, 554 and other controls are touch-activatable. Relative to display 440, display 540 generally provides additional functionality. For instance, display 540 provides the user with capabilities for monitoring and managing patient information via tab 550 and for managing system information via tab 554, in addition to viewing and managing calls and staff locations. Enhanced graphics provide selective highlighting or shading. For instance, buttons 560 are shown in a muted or faded shade to quickly indicate to the user that those features are currently unavailable. A touch activated volume control 556 and held control 558 are also provided on the display screen 540.

Figure 15:
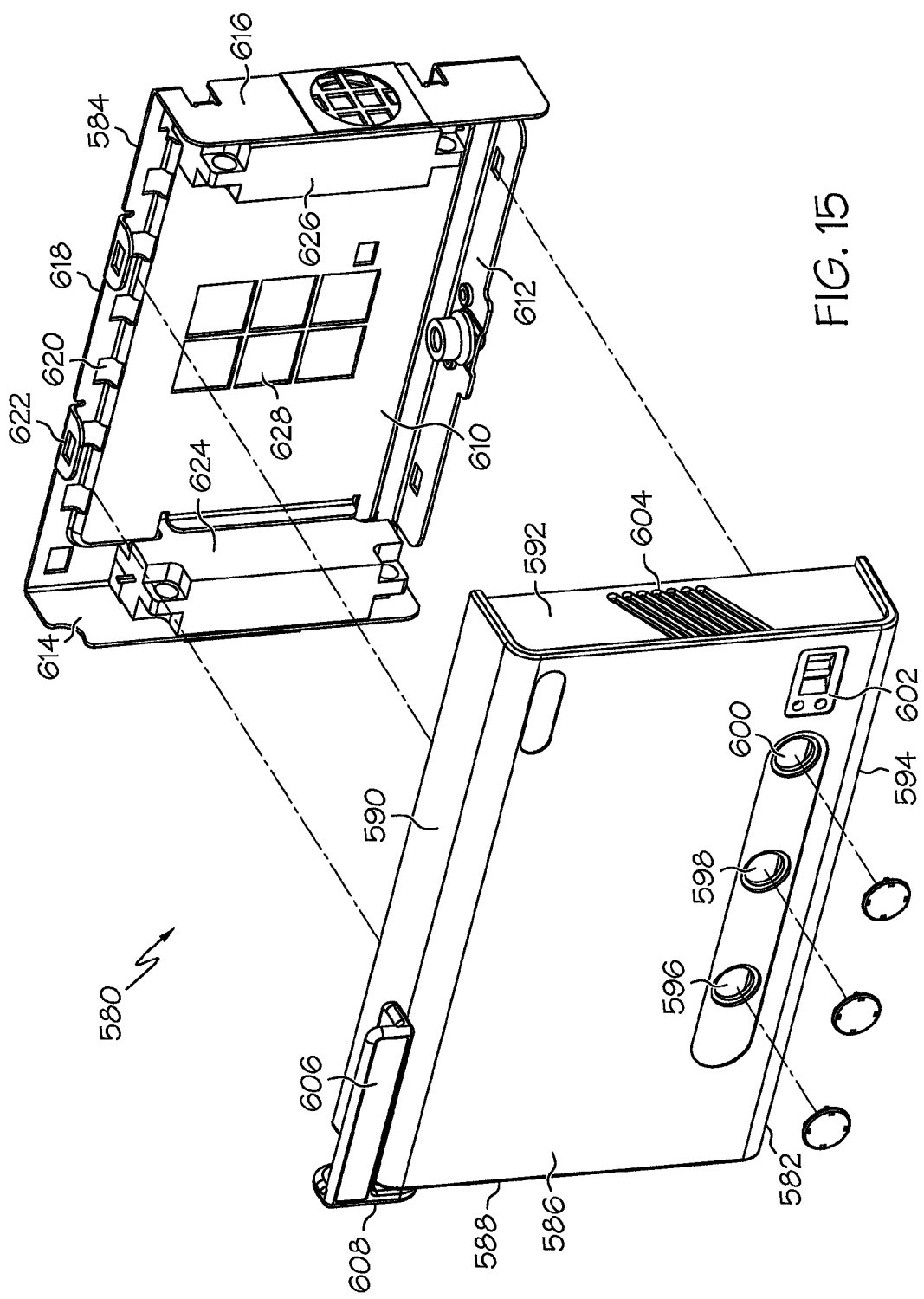
FIG. 15 is an exploded front perspective view of a user station including a first housing portion having a front face, a plurality of buttons and visual indicators supported by the front face, a code call lever positioned along the top side of the first housing portion, a speaker grill in a least one of the laterally spaced sides of the first housing portion, a second housing portion including a back face and a pair of laterally spaced sides, and a pair of speakers, each mounted to one of the laterally spaced sides.

FIG. 15 is an exploded front perspective view of a user station 580, which is similar to stations 400 and 530 but without the graphical display capabilities. Perspective views of an embodiment similar to station 580, showing the front face and sides, and including a microphone and call placed indicator supported by the front face, are shown in FIGS. 29-31. A back elevational view of user station 580 showing a plurality of connector ports to connect a variety of devices, equipment and/or services to the user station is shown in FIG. 32.

Exemplary embodiments of station 580 are IBM Part No. 43T2082 and IBM Part No. 43T1862. Station 580 includes a first housing portion 582 having a front face 586, a plurality of apertures 596, 598, 600 proximate bottom side 594 and configured for installation of capacitive touch actuators, a code call lever 606 positioned along the top side 590 of the first housing portion 582, a speaker grill 604 in a least one of the laterally spaced sides 588, 592 of the first housing portion 582, and an infrared receiver 602 configured to receive infrared signals from tags or badges emitting IR signals for locating and tracking of staff and/or equipment throughout the healthcare communication system. Lever 606 is pivotably mounted to side 588 by lever mount 608.

Second housing portion 584 attaches to first housing portion 582 by couplers 622. Second housing portion 584 includes a plurality of mounting slots 620 (FIG. 15) configured to receive mounting fingers 646 of a universal mounting plate 640 (FIG. 16) as described below and shown in FIGS. 15 and 16. A pair of speakers 624, 626 are mounted to sides 614, 616 respectively. A plurality of apertures 628 are provided in element 610 to receive a plurality of mounting ports to connect station 580 to the healthcare communication system, computer networks, other computing devices and accessories, such as a computer mouse, keyboard, camera, external video monitors with touch capability, or the like. Dual side mounted speakers allow sound to be projected out both sides to make it easier to be heard, and also results in a "clean" front face to make the station easier to clean. The capacitive touch actuators also eliminate the need for physical buttons and results in a smoother cleanable surface.

Figure 16:
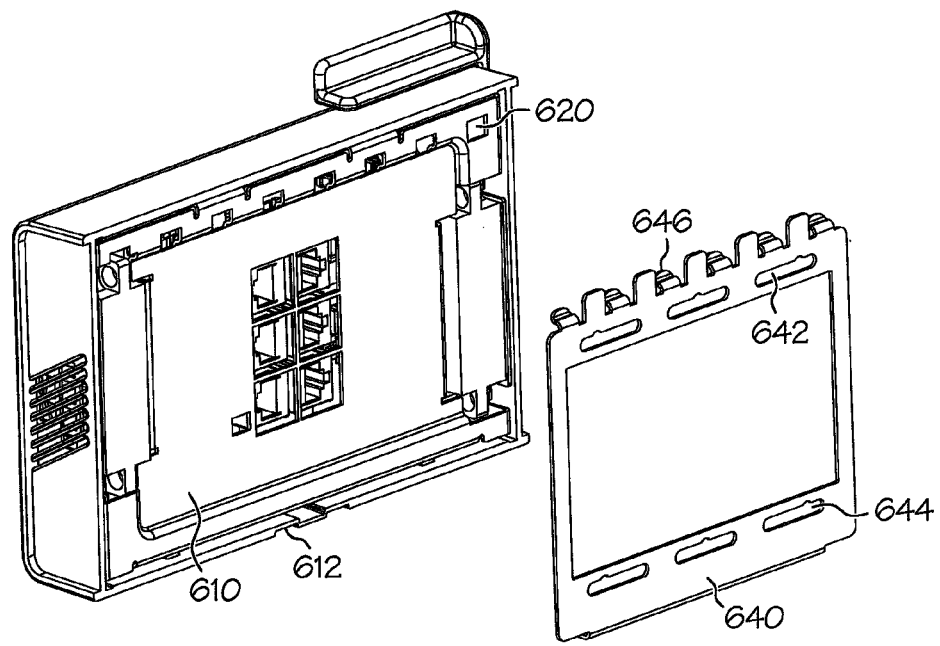
FIG. 16 is an exploded rear perspective view of a portion of the user station of FIG. 15, showing a universal mounting plate and connector slots in a rear portion of the housing.

FIG. 16 is an exploded rear perspective view of a portion of the user station 580 of FIG. 15, showing a universal mounting plate 640 and mounting slots 620 in a rear portion of the housing 612, laterally spaced to align with prongs or fingers 646 of mounting plate 640. Mounting plate 640 also includes a pair of longitudinally spaced laterally elongated mounting slots 642, 644. Another view of mounting plate 640 is shown in FIG. 33 of U.S. Provisional Patent Application Ser. No. 61/066,882, filed Feb. 22, 2008.

Mounting plate 640 is configured to mount any of the user stations 400, 530, 580 to a wall outlet box or back box. The flexible mounting design allows stations to be installed onto 2-gang, 3-gang, or 4-gang outlet boxes with continuous, side to side adjustment capability. Flexible mounting may reduce installation costs for a facility, since whatever configuration of back boxes is already installed may be used to mount the stations. The flexible mounting design also overcomes wall construction discrepancies and tolerances, in addition to providing flexibility to use one of several sizes of back boxes. The flexible mounting also enables wall mountable user stations to "nest" with other wall-mountable system components, such as bed connector units (e.g., an Audio Station Bed Connector or ASBC) so that both the station and the other unit can be mounted side by side to one mounting box. The nested mounting configuration enabling one-box mounting of these components may reduce installation costs, since only one back box is required to mount both the user station and the other unit.

Figure 17:
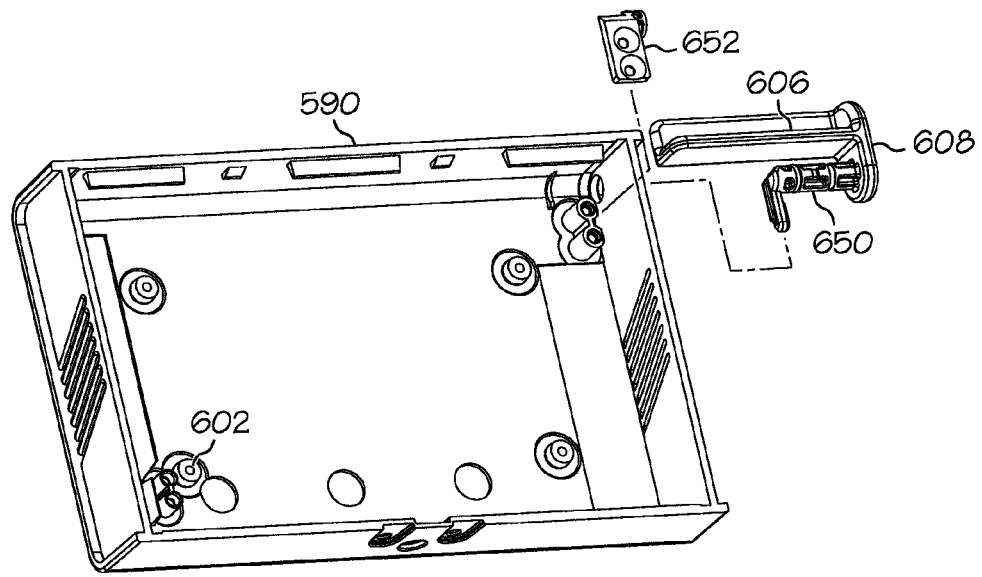
FIG. 17 is a rear exploded perspective view of the first housing portion of the user station of FIG. 15, showing a code call lever and a coupler to pivotably couple the code lever to the housing.

FIG. 17 is a rear exploded perspective view of the first housing portion 590 of the user station 580 of FIG. 15, showing a code call lever 606 and a coupler 608, 650, 652 to pivotably couple the code call lever to the housing. The side-mounting configuration of call lever 606 provides the code blue call lever functionality without degrading the appearance of the front face of the station when the call lever option is not included. Thus, the same housing may be used whether or not the station will provide the code call lever. Also, the side mounting removes the lever from the front face, aiding in the cleanability of the front face.

Figure 18:
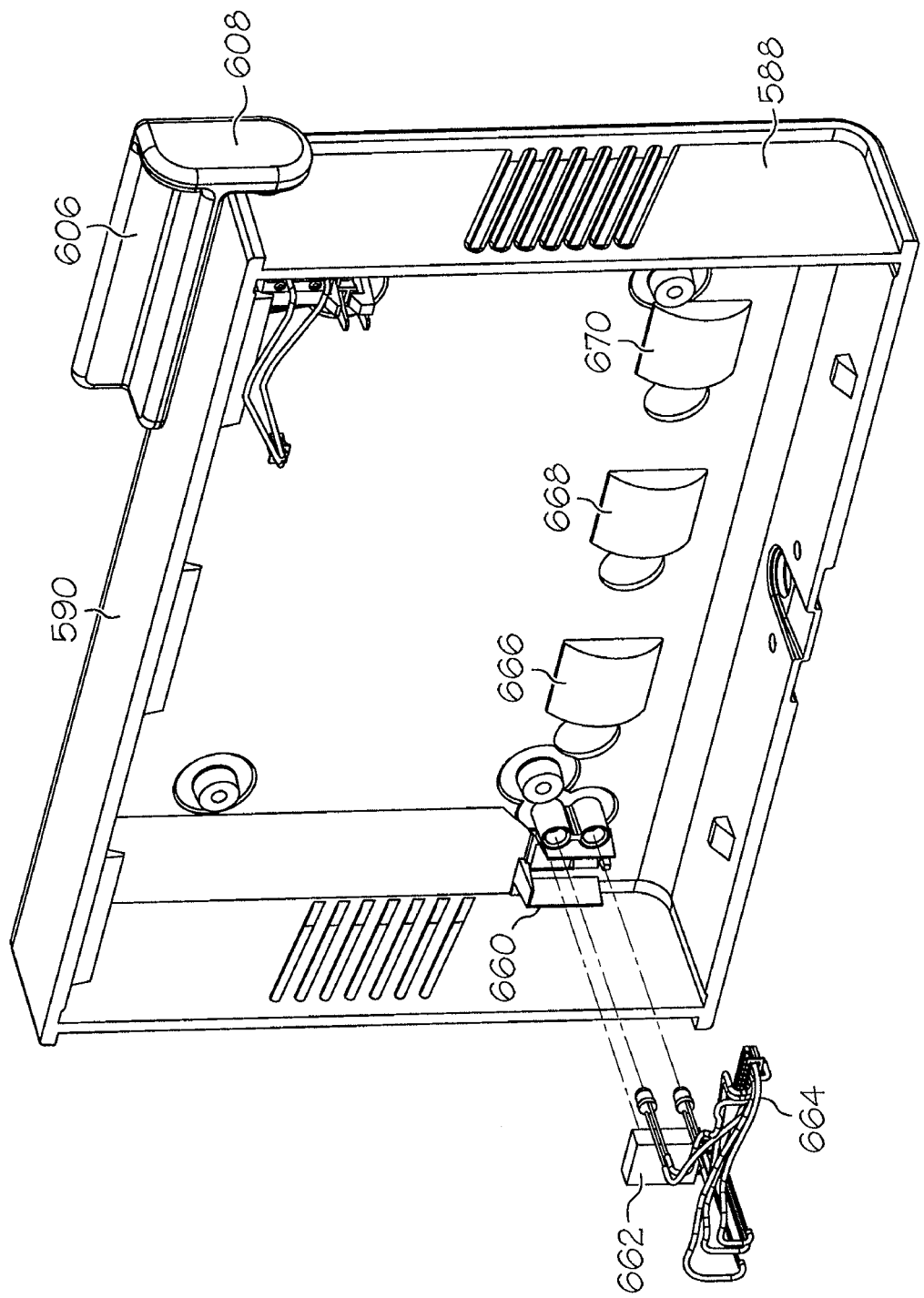
FIG. 18 is another rear exploded perspective view of the first housing portion of the user station of FIG. 15, showing a plurality of touch switches supported by the first housing portion, an infrared sensor and mounting apparatus for securing the infrared sensor in the housing, the code call lever supported by the top side and pivotably coupled to one of the laterally spaced sides of the first housing portion, and speaker grills on each of the laterally spaced sides of the first housing portion.

FIG. 18 is another rear exploded perspective view of the first housing portion 590 of the user station 580 of FIG. 15, showing a plurality of touch switches 666, 668, 670 supported by the first housing portion 590, an infrared locating sensor assembly 662, 664 and mounting apparatus 660 for securing the infrared sensor in the housing, the code call lever 606 supported by the top side and pivotably coupled to one of the laterally spaced sides of the first housing portion by coupling portion 608, and speaker grills on each of the laterally spaced sides 588, 592 of the first housing portion.

Figure 19:
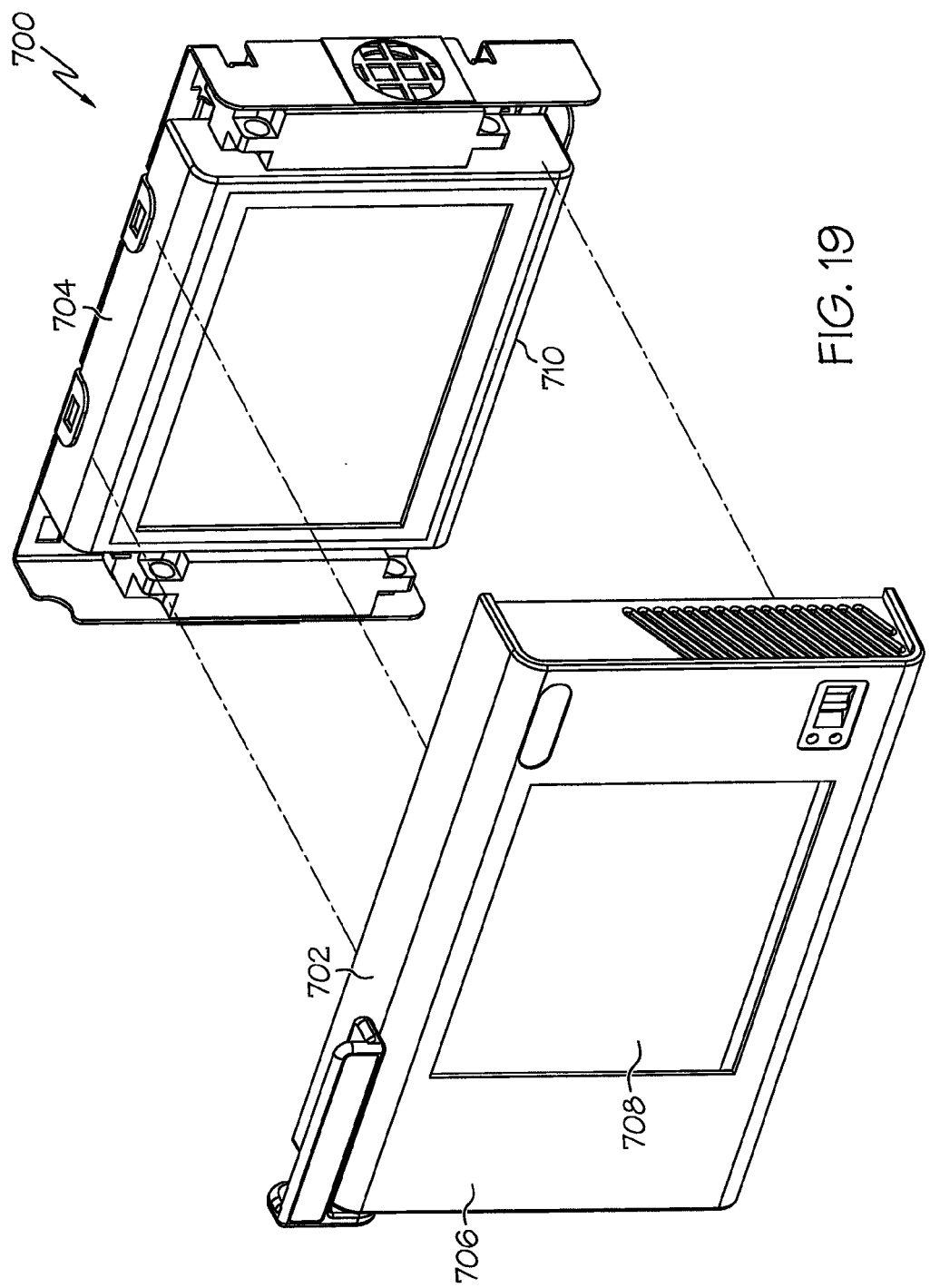
FIG. 19 is a front exploded perspective view of another embodiment of a user station, similar to the embodiment of FIG. 9, having a first housing portion configured to support a code call lever, an infrared sensor and having an aperture sized to receive a graphical touch display, and a second housing portion configured to support the graphical touch display and a pair of laterally spaced speakers.

FIG. 19 is a front exploded perspective view of another embodiment 700 of a user station, similar to the embodiment of FIG. 9, having a first housing portion 702 configured to support a code call lever, an infrared sensor and having an aperture 708 sized to receive a graphical touch display 710. A second housing portion 704 is configured to support the graphical touch display 710 and associated circuitry, as well as a pair of laterally spaced speakers as described above.

Figure 20:
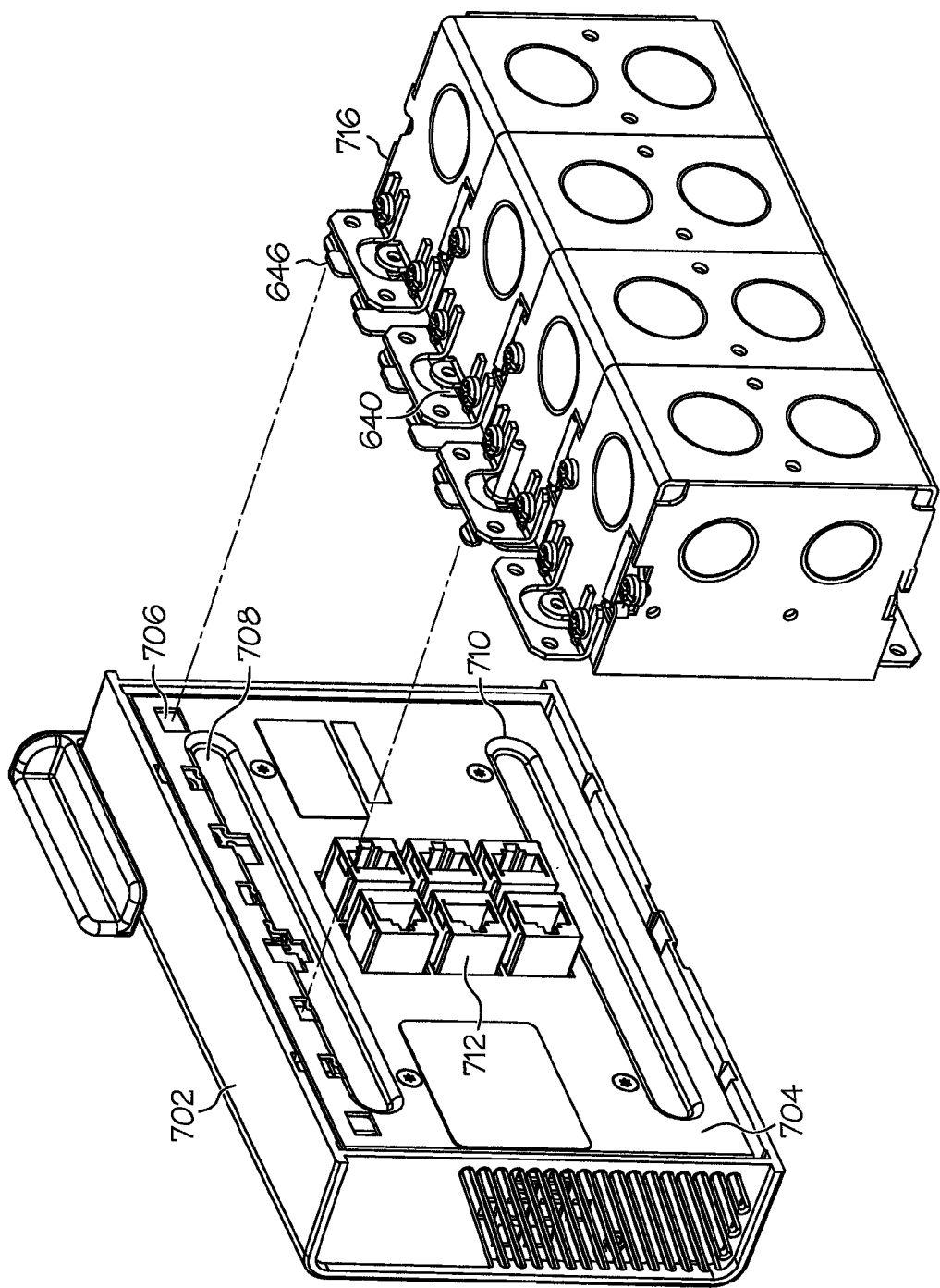
FIG. 20 is a rear exploded perspective view of the user station of FIG. 19, a mounting apparatus, and a mounting box configurable to mount the user station to a vertical structure, the user station including a plurality of slots configured to receive fingers of the mounting apparatus, the user station including a plurality of connector ports configurable to connect a variety of computing devices and computer accessories to the user station.
Figure 21:
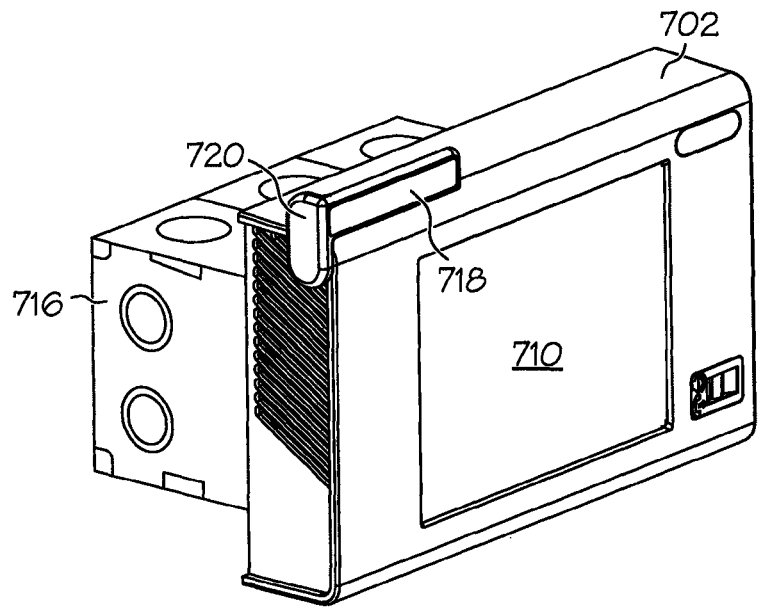
FIG. 21 is a front perspective view of the user station of FIG. 19 mounted to the mounting box.

FIG. 20 is a rear exploded perspective view of the user station 700 of FIG. 19, a mounting apparatus 640 including a plurality of fingers 646 configured to engage slots 706 of housing 702 to couple station 700 to a mounting box 716, which is configurable to mount the user station 700 to a vertical structure. User station 700 includes a plurality of connector ports 712 configurable to connect a variety of computing devices and computer accessories to the user station, for example, video and touch adapters to allow the connection of external video monitors and touch capability, USB ports to attach computer accessories, a PoE port, and the like. FIG. 21 is a front perspective view of the user station 700 of FIG. 19 mounted to the mounting box 716. Mounting apparatus 640 is configured to be able to mount a variety of embodiments of user stations to a variety of different mounting boxes.

User station 700 includes a graphical display 710 and, optionally, a code call lever 718 mounted to housing 702 by mounting portion 720. Graphical display 710 may be of one of the types described above in connection with the descriptions of stations 400, 530, 470, 500.

Figure 22:
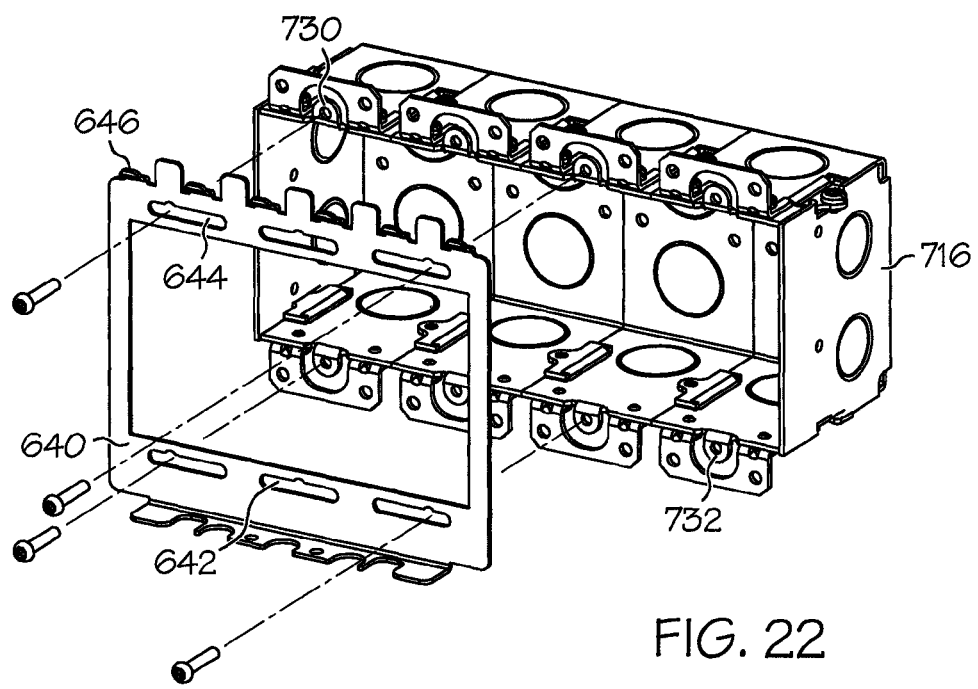
FIG. 22 is a front exploded perspective view of the mounting apparatus of FIG. 20, having a top side and a bottom side longitudinally spaced from the top side, a plurality of mounting fingers arranged laterally along the top and bottom sides, and a pair of laterally elongated mounting slots provided in the top and bottom sides; and showing a mounting box including a plurality of mounting ports on a top side and a plurality of mounting ports on a bottom side longitudinally spaced from the top side.

FIG. 22 is a front exploded perspective view of the mounting apparatus 640 of FIG. 20, having a top side and a bottom side longitudinally spaced from the top side, a plurality of mounting fingers 646 arranged laterally along the top and bottom sides, and a pair of laterally elongated mounting slots 642, 644 provided in the top and bottom sides as described above. Screws or other fasteners insert into slots 642, 644 of apparatus 640 and mounting ports 730, 732 of mounting box 716, while fingers 646 couple to the user station housing as described above, to couple the station to the box. The mounting box includes a plurality of mounting ports 730 on a top side and a plurality of mounting ports 732 on a bottom side longitudinally spaced from the top side.

Figure 23:
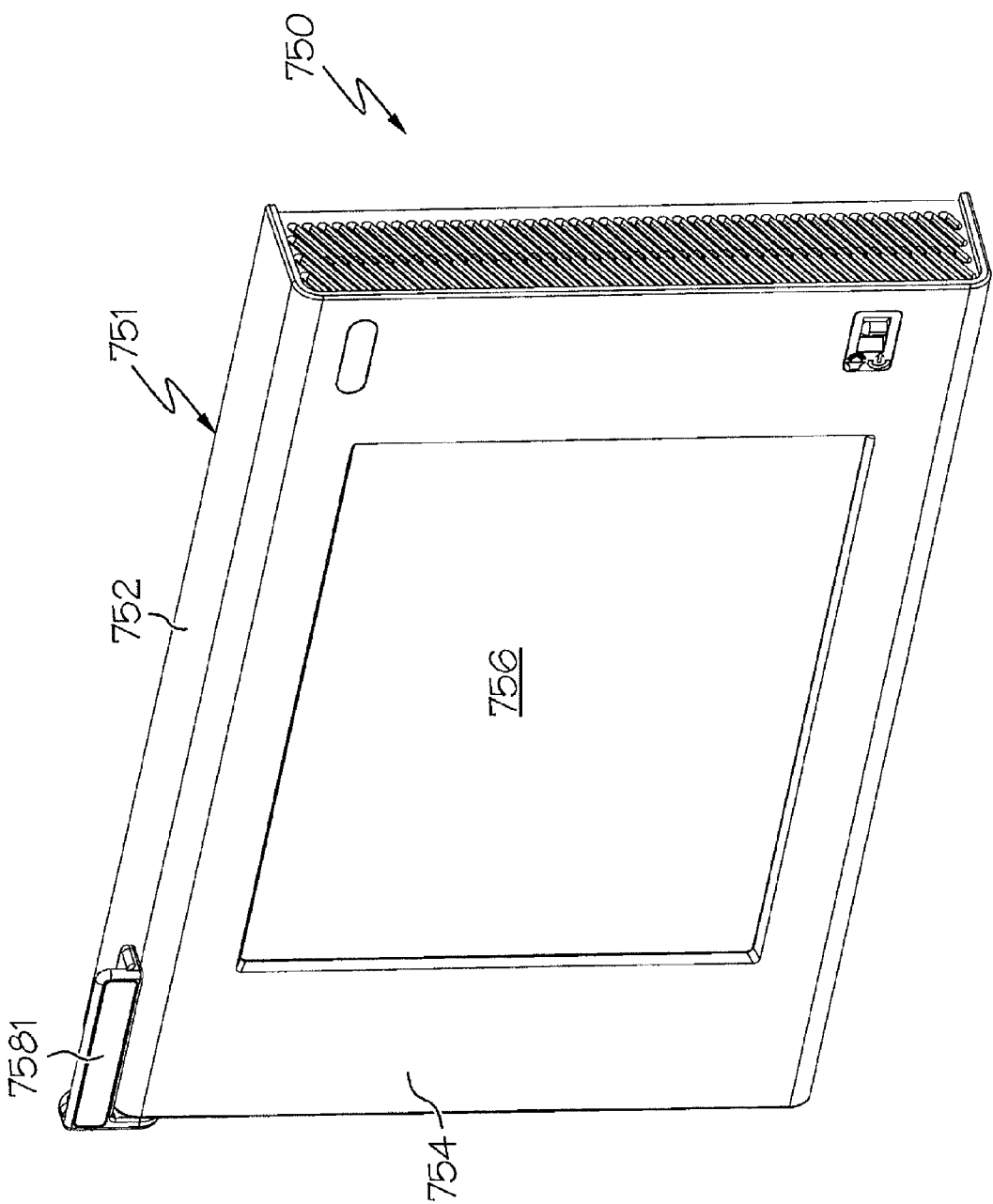
FIG. 23 is a front perspective view of another embodiment of a user station, similar to the embodiment of FIG. 13, including a housing having a front face, a rear face, a top side, a bottom side longitudinally spaced from the top side, a first side and a second side laterally spaced from the first side, the front face including an aperture sized to receive an enlarged graphical touch display, a code call lever positioned above the top side, and a speaker grille located in at least one of the laterally spaced sides.

FIG. 23 is a front perspective view of another embodiment of a user station 750, similar to the embodiment of FIG. 13, including a housing portion 751 having a front face 754, a rear face spaced from the front face, a top side 752, a bottom side longitudinally spaced from the top side, a first side and a second side laterally spaced from the first side to define an interior region. The front face 754 includes an aperture 756 sized to receive an enlarged graphical touch display as described above. Front face 754 optionally supports a code call lever 7581 positioned above the top side, and a speaker grille located in at least one of the laterally spaced sides. Station 750 has similar graphical capabilities as stations 470, 500, 530 described above. Relative to station 700, the graphical display of station 750 generally takes up a larger area of the front face.

Figure 24:
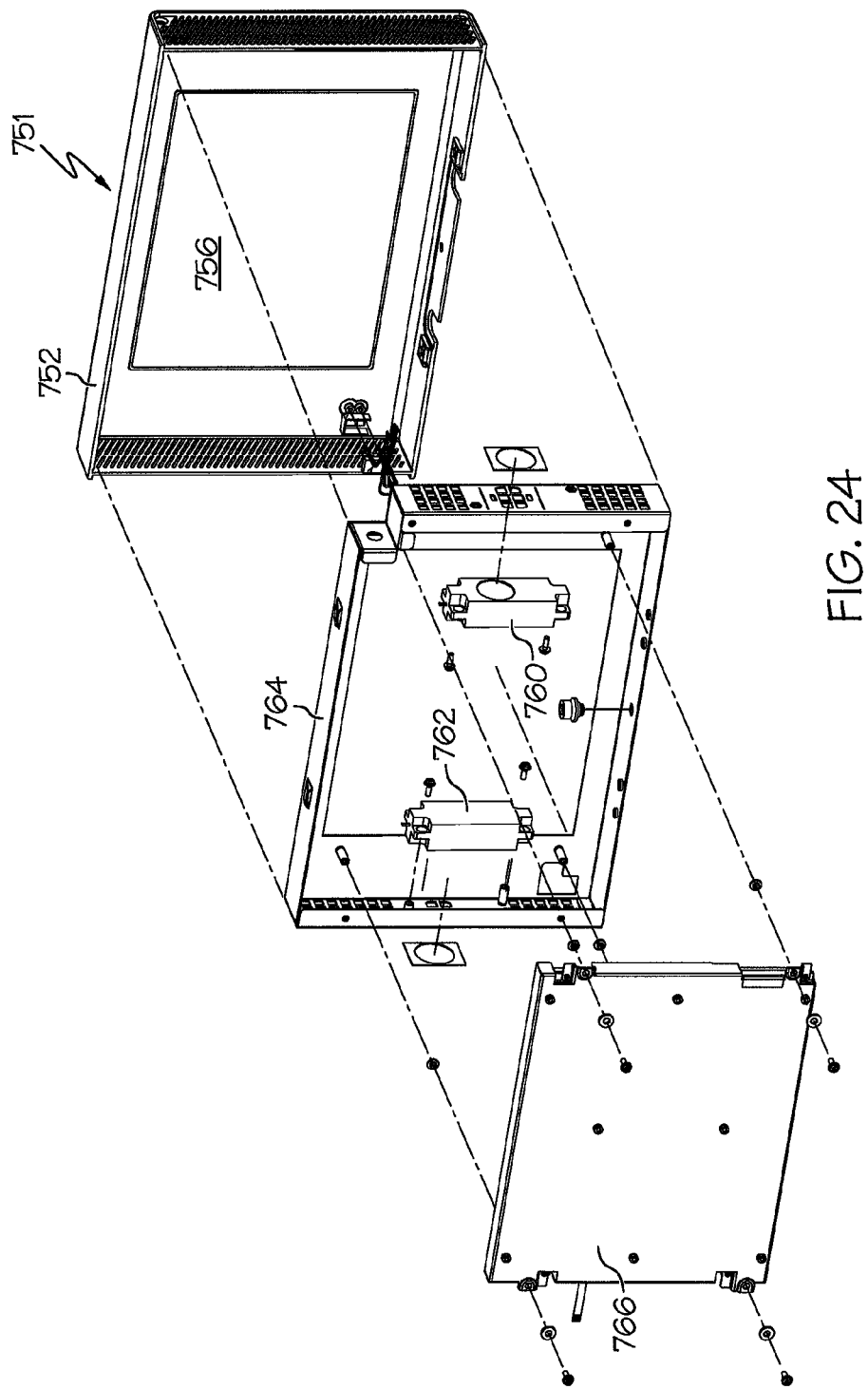
FIG. 24 is a rear exploded view of a portion of the user station of FIG. 23, including a first housing portion, a second housing portion insertable in the first housing portion, and a touchscreen display assembly mountable to the first housing portion, the second housing portion having a pair of speakers mounted to laterally spaced sides thereof.

FIG. 24 is a rear exploded view of a portion of the user station 750 of FIG. 23, including the first housing 751 that includes top side 752, a second housing portion 764 insertable in the first housing portion 751 that includes top side 752, and a touchscreen display assembly 766. The second housing portion 764 has a pair of speakers 760, 762 mounted to laterally spaced sides thereof.

Figure 25:
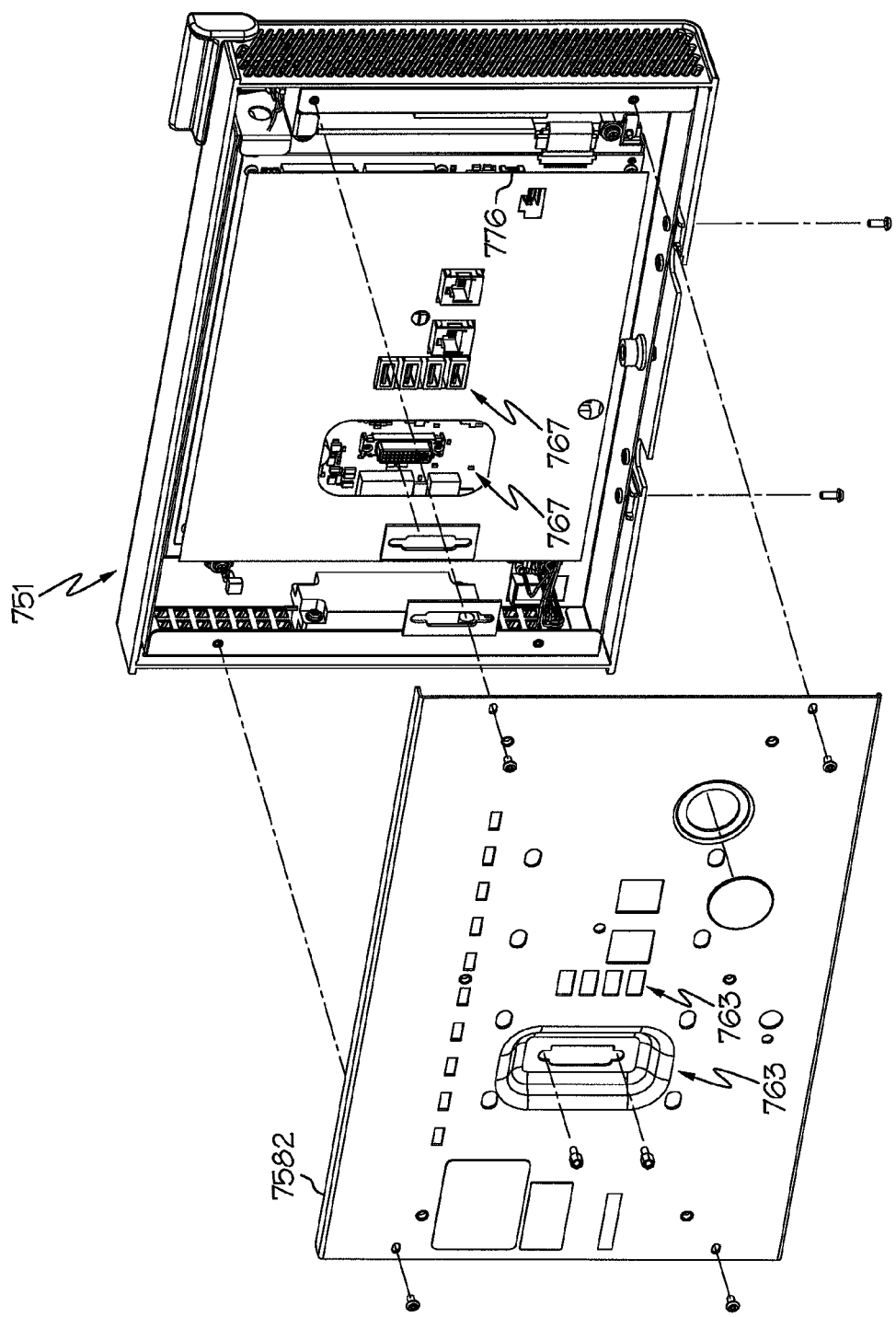
FIG. 25 is a second rear exploded view of another portion of the user station of FIG. 23, showing components mounted to touchscreen display and a rear housing portion.
Figure 26:
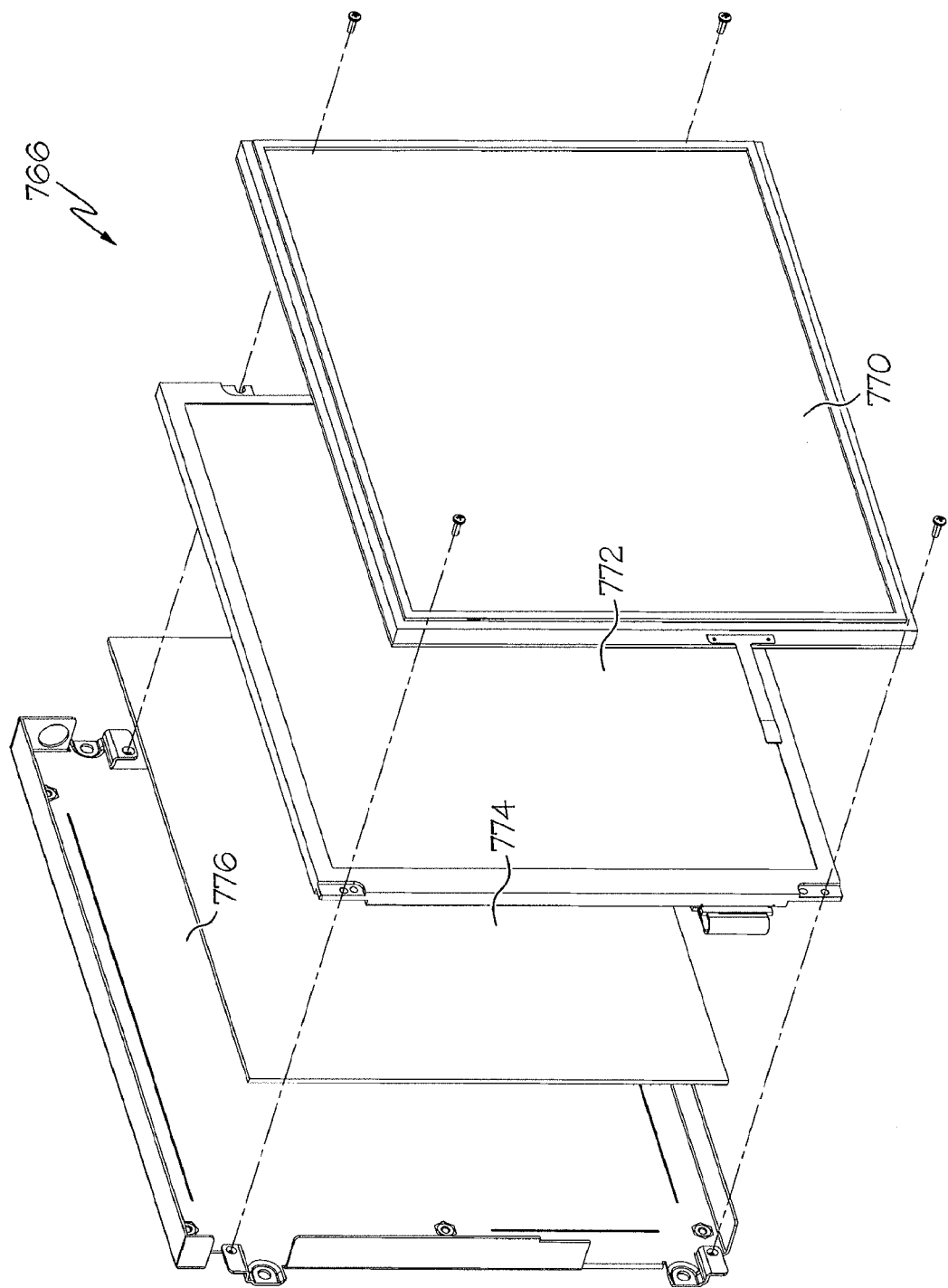
FIG. 26 is a front exploded perspective view of the touchscreen display assembly of FIGS. 24-25.

FIG. 25 shows the first housing portion 751 that includes top side 752 with second portion 764 and touchscreen assembly 766 installed therein (but not visible in FIG. 25). A printed circuit board assembly 776 shown in FIG. 26 includes componentry relating to touchscreen assembly 766, as well as other computer circuitry configured to operate the features and functions described herein. A plurality of connectors are provided as described above. Rear cover 7582 includes a plurality of apertures 763 of varying sizes to accommodate devices, cabling and wiring connectable to ports 767. Touchscreen assembly 766 includes a touch sensor panel 770, an LCD display 772 (i.e., VGA or SVGA), an insulator 774 and the printed circuit board assembly 776 as described above and as shown in FIG. 26.

Figure 27:
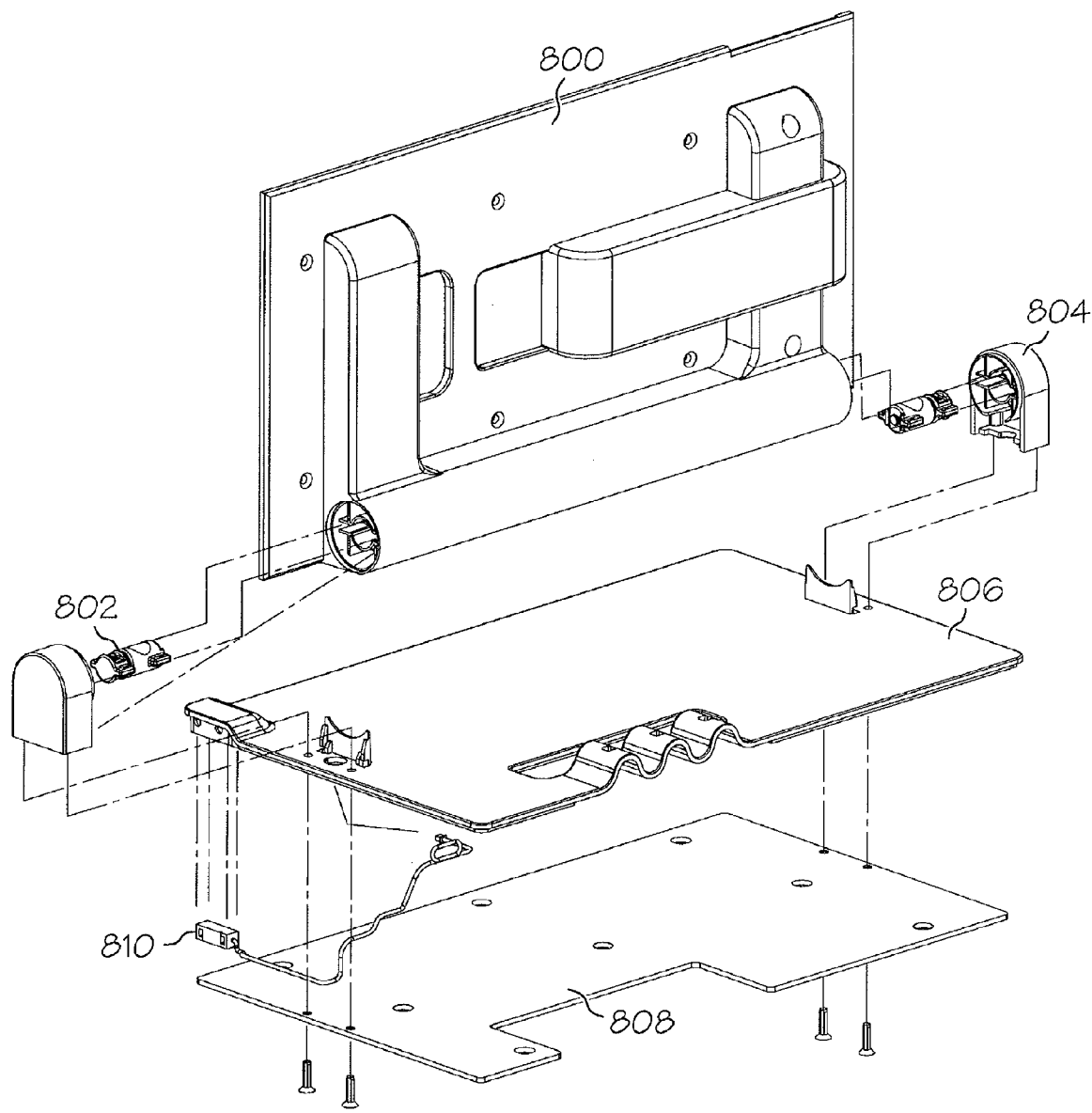
FIG. 27 is a rear exploded perspective view of a back housing portion for a desk mounted user station similar to FIG. 12, including a rear cover, a microphone, a pivot connector and a mounting stand.
Figure 28:
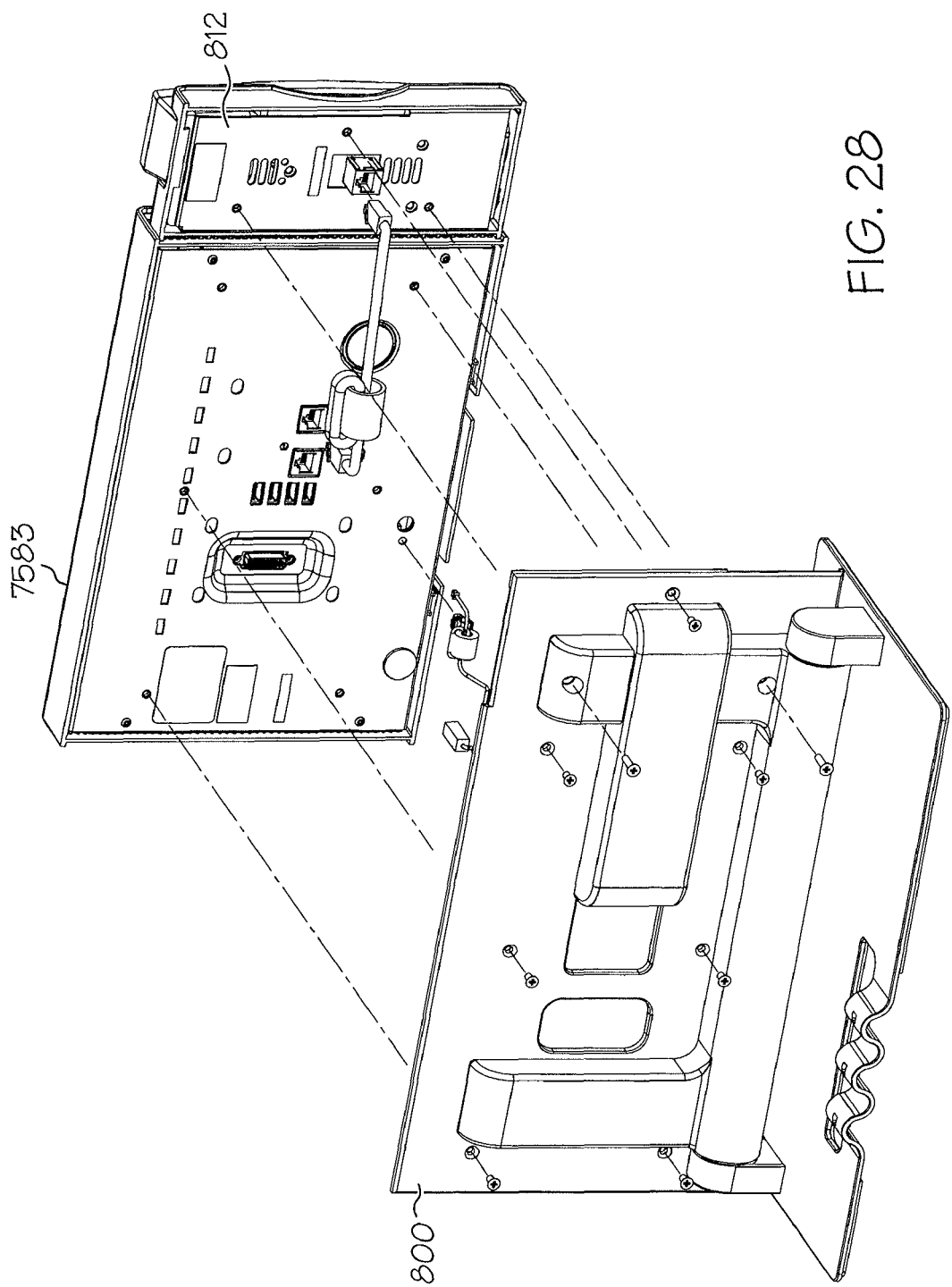
FIG. 28 is another rear exploded perspective view of the back housing portion of FIG. 27, showing the back cover, mounting stand, a back portion of the user station housing mountable to the back cover, the back portion of the user station including a plurality of connector ports, and a handset cradle assembly mountable to the back cover.

FIGS. 27-28 are rear exploded perspective views of a back housing portion 800 for a desk mounted user station similar to FIG. 12, including a rear cover 800, a microphone 810, a pivot connector 802, 804 (such as a friction hinge) and a mounting stand 806, 808. FIG. 28 shows the back cover 800, mounting stand 806, user station assembly 7583 mountable to back cover 800 by screws or other fasteners, and a back portion of a telephone handset cradle assembly 812 mountable to the back cover 800 adjacent the station 7583. In general, housing portions and components described herein are made of a plastic, such as PC/ABS plastic or similar material.

In the desk mounted configuration of the above-described user stations, microphone 810 is a base mounted directional microphone. The base mounted directional microphone focuses the reception of the user's voice in a conical region directly in front of the station while limiting the reception of other voices and noise outside the conical region. In the wall or vertically mountable configurations of the above-described user stations, an underside mounted microphone is used. The microphone is located on the main user station assembly on the bottom edge (facing downward) underneath the display. The underside mounted microphone allows the station to pick up voices and other sounds around the mounting location. The underside microphone also reduces the likelihood of damage due to user contact and fluids or other contaminants.

In general, the user stations described herein are configurable and scalable, such that features described with reference to one embodiment may be incorporated into other embodiments as well.

The Appendices filed with U.S. Provisional Patent Application Ser. No. 61/066,882 contain additional details relating to features of the subject matter disclosed herein.

The present disclosure describes patentable subject matter with reference to certain illustrative embodiments. The drawings are provided to facilitate understanding of the disclosure, and may depict a limited number of elements for ease of explanation. Except as may be otherwise noted in this disclosure, no limits on the scope of patentable subject matter are intended to be implied by the drawings. Variations, alternatives, and modifications to the illustrated embodiments may be included in the scope of protection available for the patentable subject matter.

The invention claimed is:

1. A healthcare communication system comprising
   a primary console having a first housing, a first touchscreen display coupled to the first housing, and a telephone handset adjacent the touchscreen display, and
   a plurality of secondary consoles, each secondary console being located in a respective patient room of a plurality of patient rooms, each secondary console having a respective second housing and a respective second touchscreen display coupled to the second housing, each of the secondary consoles being communicatively coupled to the primary console, wherein each secondary console of the plurality of secondary consoles includes electrical circuitry in the respective second housing, the electrical circuitry being configured to receive calls from the primary console and each of the other secondary consoles of the plurality of secondary consoles and to display information relating to the received calls on the respective second touchscreen display, wherein the electrical circuitry is configured to enable a user to place calls to other users and to select a preferred mode of calling other users, the preferred mode selected from a plurality of calling modes comprising at least one of the following: voice routing to a located position, wireless telephone, or text paging to a wireless device.

2. The healthcare communication system of claim 1, wherein the primary console serves as a nurse call computer at a master nurse station.

3. The healthcare communication system of claim 1, wherein the primary console includes a desk mount and a pivot coupler that pivotably couples the first housing to the desk mount.

4. The healthcare communication system of claim 3, wherein the telephone handset pivots relative to the desk mount along with the first housing as the first housing is pivoted relative desk mount.

5. The healthcare communication system of claim 3, further comprising a back plate that is coupled to the pivot coupler for pivoting movement and the first housing being coupled to the back plate.

6. The healthcare communication system of claim 5, further comprising a handset cradle coupled to the back plate to pivot therewith, the handset cradle being configured to support the telephone handset.

7. The healthcare communication system of claim 3, wherein the pivot coupler comprises a friction hinge.

8. The healthcare communication system of claim 1, further comprising at least one Power over Ethernet (POE) switch and wherein the plurality of secondary consoles are communicatively coupled to the primary console via the at least one POE switch.

9. The healthcare communication system of claim 1, further comprising a plurality of dome light assemblies that each have circuitry and wherein the plurality of secondary consoles are communicatively coupled to the primary console via the circuitry of the plurality of dome light assemblies.

10. The healthcare communication system of claim 1, wherein each of the first and second touchscreen displays each comprising one or more of the following:
    a high resolution touch display, a Super Video Graphics Array (SVGA) display, and at least one touch actuator.

11. The healthcare communication system of claim 1, wherein the electrical circuitry is configured to display first and second windows on the respective second touchscreen display, to display the information relating to the received calls in the first window, and to display at least one of staff information and patient information in the second window.

12. The healthcare communication system of claim 1, wherein the second touchscreen display of each of the plurality of secondary consoles is configured to display visual cues relating to at least one of the received calls.

13. The healthcare communication system of claim 12, wherein the second touchscreen display of each of the plurality of secondary consoles is configured to display a first visual cue relating to a first received call in a first color and display a second visual cue relating to a second received call in a second color.

14. The healthcare communication system of claim 12, wherein at least one of the visual cues comprises a graphical icon.

15. The healthcare communication system of claim 1, further comprising at least one staff console located outside the plurality of patient rooms, the at least one staff console being communicatively coupled to the primary console.

16. The healthcare communication system of claim 15, further comprising at least one Power over Ethernet (POE) switch and wherein the at least one staff console is communicatively coupled to the primary console via the at least one POE switch.

* * * * *

UNITED STATES PATENT AND TRADEMARK OFFICE
CERTIFICATE OF CORRECTION

PATENT NO. : 9,235,979 B2  
APPLICATION NO. : 14/453009  
DATED : January 12, 2016  
INVENTOR(S) : Richard J. Schuman, Sr. et al.

Page 1 of 1

It is certified that error appears in the above-identified patent and that said Letters Patent is hereby corrected as shown below:

Claims

1. Claim 4, Col. 18, Line 39, the phrase "relative desk" should be corrected to --relative to the desk--.

2. Claim 9, Col. 18, Line 56, the term "dome light" should be corrected to --indicator--.

3. Claim 9, Col. 18, Line 58, the term "dome light" should be corrected to --indicator--.

4. Claim 10, Col. 18, Line 61, the phrase "wherein each of the" should be corrected to --wherein the--.

Signed and Sealed this  
Nineteenth Day of April, 2016

Michelle K. Lee  
*Director of the United States Patent and Trademark Office*